US011980703B2

(12) United States Patent
Richard et al.

(10) Patent No.: US 11,980,703 B2
(45) Date of Patent: May 14, 2024

(54) DISPENSER WITH AN IMPROVED HEATER ARRANGEMENT

(71) Applicant: S. C. JOHNSON & SON, INC., Racine, WI (US)

(72) Inventors: Jesse Richard, Racine, WI (US); Michael Haynes, Muskego, WI (US); David Dycher, Shenzhen (CN); Harold Augier, Zhongshan (CN)

(73) Assignee: S. C. JOHNSON & SON, INC., Racine, WI (US)

( * ) Notice: Subject to any disclaimer, the term of this patent is extended or adjusted under 35 U.S.C. 154(b) by 17 days.

(21) Appl. No.: 17/977,064

(22) Filed: Oct. 31, 2022

(65) Prior Publication Data
US 2023/0048941 A1 Feb. 16, 2023

Related U.S. Application Data

(63) Continuation of application No. 16/743,939, filed on Jan. 15, 2020, now Pat. No. 11,554,191.

(51) Int. Cl.
*A61L 9/03* (2006.01)
*A61L 9/12* (2006.01)
*B01F 23/21* (2022.01)

(52) U.S. Cl.
CPC ............ *A61L 9/037* (2013.01); *A61L 9/127* (2013.01); *A61L 2209/133* (2013.01); *A61L 2209/134* (2013.01); *B01F 23/215* (2022.01)

(58) Field of Classification Search
CPC ......... A61L 9/037; A61L 9/127; B01F 23/215
See application file for complete search history.

(56) References Cited

U.S. PATENT DOCUMENTS

| | | | |
|---|---|---|---|
| 6,697,571 B2 | 2/2004 | Triplett et al. |
| 6,968,124 B1 | 11/2005 | Varanasi et al. |
| 7,032,831 B2 | 4/2006 | Duston et al. |
| 7,840,123 B2 | 11/2010 | Belongia et al. |
| 8,301,019 B2 | 10/2012 | Smith et al. |

(Continued)

FOREIGN PATENT DOCUMENTS

| | | | |
|---|---|---|---|
| EP | 0942648 B9 | 9/1999 |
| EP | 1108358 A1 | 6/2001 |
| WO | 2020119926 A1 | 6/2020 |

OTHER PUBLICATIONS

International Search Report from corresponding PCT Application No. PCT/US2021/012909, dated May 11, 2021 (3 pages).

(Continued)

*Primary Examiner* — Robert A Hopkins
(74) *Attorney, Agent, or Firm* — Quarles & Brady LLP

(57) ABSTRACT

A volatile material dispenser includes a housing that defines a longitudinal axis and is configured to receive a refill containing a volatile material and a wick. The volatile material dispenser also includes a cylinder that includes an inner wall that defines an opening and an interior edge, a resistor embedded in the cylinder, and a heater chassis that includes an inner wall that defines a passage between an upper end and a lower end. The upper end of the heater chassis abuts the interior edge of the cylinder. In addition, the inner wall of the cylinder extends away from the longitudinal axis at a first angle and the inner wall of the heater chassis extends away from the longitudinal axis at a second angle.

40 Claims, 20 Drawing Sheets

(56) References Cited

U.S. PATENT DOCUMENTS

| | | |
|---|---|---|
| 8,821,171 B2 | 9/2014 | Belongia |
| 8,858,236 B2 | 10/2014 | Richard |
| 8,983,279 B2 * | 3/2015 | Adair .................. H05B 1/0225 |
| | | 392/395 |
| 9,669,126 B2 | 6/2017 | Jaworski et al. |
| 10,543,292 B2 | 1/2020 | Lal et al. |
| 10,973,944 B1 | 4/2021 | Farrell et al. |
| 2003/0194355 A1 | 10/2003 | Pedrotti et al. |
| 2004/0247301 A1 | 12/2004 | Yip et al. |
| 2011/0139885 A1 | 6/2011 | Gasper et al. |
| 2012/0275772 A1 | 11/2012 | Belongia |
| 2014/0034748 A1 | 2/2014 | Adair et al. |
| 2014/0037273 A1 | 2/2014 | Jaworski et al. |
| 2014/0064714 A1 | 3/2014 | Ques Ramos et al. |
| 2018/0103507 A1 | 4/2018 | Davis et al. |
| 2019/0000064 A1 | 1/2019 | Luque Vera |
| 2019/0091365 A1 | 3/2019 | Pieper et al. |
| 2020/0171190 A1 | 6/2020 | Panagopoulou et al. |

OTHER PUBLICATIONS

Written Opinion of the International Searching Authority from corresponding PCT Application No. PCT/US2021/012909, dated May 11, 2021 (5 pages).

Search Strategy Report, from corresponding PCT Application No. PCT/US2021/012909, dated May 11, 2021 (1 page).

Office Action for BR Application No. 11 2022 013963-2 dated Mar. 6, 2023.

* cited by examiner

DISPENSER WITH AN IMPROVED HEATER ARRANGEMENT

CROSS REFERENCE TO RELATED APPLICATIONS

This application claims the benefit of and priority to U.S. application Ser. No. 16/743,939, filed on Jan. 15, 2020, which is incorporated by reference herein in its entirety.

REFERENCE REGARDING FEDERALLY SPONSORED RESEARCH OR DEVELOPMENT

Not applicable.

SEQUENTIAL LISTING

Not applicable.

BACKGROUND OF THE INVENTION

1. Field of the Invention

The present disclosure relates generally to a system for dispensing a composition, and more particularly, to a dispenser that uses an improved heater arrangement.

2. Description of the Background of the Invention

Various volatile material dispensers are known in the prior art and generally include a housing with a refill inserted therein. The refill generally includes a container for holding a volatile material. In some dispensers, the volatile material is passively emitted therefrom. In other dispensers, a diffusion element is utilized to facilitate the dispensing of the volatile material. Examples of diffusion elements include heaters such as positive temperature coefficient (PTC) heaters, piezoelectric elements, fans, aerosol actuators, and the like. Regardless of the manner in which the volatile material is emitted, once the volatile material has been expended from the refill, the refill is removed by a user and replaced with a new refill.

One type of volatile material dispenser, which is sometimes referred to as a plug-in scented oil dispenser, includes a housing and a heater disposed within the housing. A refill for use with a plug-in scented oil dispenser generally includes a container with a volatile material therein and a wick in contact with the volatile material and extending out of the refill. Upon insertion of the refill into the dispenser, at least a portion of the wick is disposed adjacent the heater such that volatile material that moves through the wick is volatilized by the heater. The volatile material dispenser typically includes a plug assembly having electrical prongs extending outwardly from the housing. The electrical prongs are inserted into a standard electrical outlet and thereafter supply electrical energy to the volatile material dispenser. One such dispenser is disclosed in the commonly-assigned U.S. Pat. No. 9,669,126, which is incorporated by reference herein in its entirety. Plug-in scented oil dispensers may also utilize a fan to aid in vaporizing and dispersing volatile material.

Existing dispensers, however, experience performance issues. For example, one common issue with existing dispensers is condensation build up. That is, as a dispenser is actively or passively emitting volatile material, gas within a housing thereof may have a high relative humidity. Thus, condensation on an interior surface thereof is likely to form. Different venting systems have been used in existing dispensers in an attempt to minimize condensation formation, however, these methods do not provide a complete solution. Additionally, existing venting systems may lead to disrupting or inhibiting plume dispersion. That is, using certain prior art vent configurations, a plume released by a dispensing system may be affected negatively, which can result in sub-optimal distribution of a material by the dispensing system. Further, another problem is poor heater efficiency. More specifically, existing dispensers do not efficiently convert power into heat energy to assist in volatizing the volatile material. Therefore, a need exists for a dispenser that includes a heater arrangement that provides enhanced performance and other features to minimize condensation potential.

SUMMARY OF THE INVENTION

According to one embodiment, a heater arrangement for a volatile material dispenser includes a cylinder defining an opening and a resistor embedded in the cylinder. The dispenser includes a housing configured to receive a refill containing a volatile material and a wick, and the housing includes a first cavity configured to support the heater arrangement. Further, the dispenser is configured such that, when the refill is received within the housing, the opening receives the wick therein so that a radial gap is formed between the heater arrangement and the wick.

According to another embodiment, a volatile material dispenser includes a housing configured to receive a refill containing a volatile material and a wick, wherein the housing includes a first cavity supporting a heater arrangement. The heater arrangement includes a cylinder, a heater chassis, and a resistor that is embedded in the cylinder. The cylinder defines an opening, and the heater chassis defines a passage that is configured to be axially aligned with the opening of the cylinder. The dispenser is configured such that, when the refill is received within the housing, the opening of the cylinder is axially aligned with the wick, and a radial gap is formed between the heater arrangement and the wick.

According to still another embodiment, a volatile material dispenser includes a housing configured to receive a refill containing a volatile material and a wick. The housing has a heater arrangement configured to volatize the volatile material into a vapor plume. The volatile material dispenser further includes a top cover comprising an annular wall having a first surface, a second surface, an outer edge, and an inner edge defining a central aperture for emission of volatile material therethrough. The inner edge is elevated relative to the outer edge. The heater arrangement comprises a resistor retained within a cylinder and a heater chassis that defines a passage therethrough. Further, the cylinder comprises a main surface and a chimney that defines an opening, wherein the chimney may be elevated relative to the main surface of the cylinder and gradually restricts from a first end proximate the main surface to a second end distal the main surface. The cylinder is coupled to the heater chassis and makes up less than 40% a volume of the heater arrangement. Additionally, the dispenser is configured such that, when the refill is received within the housing, the wick is axially aligned with the central aperture of the top cover, the opening of the cylinder, and the passage of the heater chassis, and the wick extends through the passage of the heater chassis and into the opening of the cylinder so that a distal end of the wick sits below the second end of the cylinder.

According to yet another embodiment, a volatile material dispenser includes a housing and a top cover. The housing is configured to receive a refill containing a volatile material and a wick and includes a first cavity supporting a heater arrangement. The top cover is configured to couple to the housing and defines a central aperture through which a vapor plume exits the housing. Further, the top cover includes an annular wall having a first surface, a second surface opposite therefrom, an outer edge, and an inner edge that defines a central aperture, wherein the central aperture defines an axial direction. The outer edge and the inner edge are concentric and are disposed on different planes. The second surface extends radially inward from the outer edge curving in a first axial direction until a trough and gradually curves in a second direction opposite the first axial direction until it meets the inner edge. Further, the dispenser is configured such that, when the top cover is coupled to the housing, the second surface faces the first cavity.

In some aspects, a volatile material dispenser includes a housing that defines a longitudinal axis and is configured to receive a refill containing a volatile material and a wick. The volatile material dispenser also includes a cylinder that includes an inner wall that defines an opening and an interior edge, a resistor embedded in the cylinder, and a heater chassis that includes an inner wall that defines a passage between an upper end and a lower end. The upper end of the heater chassis abuts the interior edge of the cylinder. In addition, the inner wall of the cylinder extends away from the longitudinal axis at a first angle and the inner wall of the heater chassis extends away from the longitudinal axis at a second angle.

In some embodiments, the first angle and the second angle are identical. In some embodiments, the first angle and the second angle are different. In some embodiments, the inner wall of the cylinder includes at least one inflection point between the opening and the interior edge. In some embodiments, the inner wall of the heater chassis includes at least one inflection point between the upper end and the lower end. In some embodiments, a first diameter of the passage at the upper end is smaller than a second diameter of the passage at the lower end. In some embodiments, the dispenser is configured such that, when the refill is received within the housing, the opening of the cylinder is axially aligned with the wick, and a radial gap is formed between the cylinder and a distal portion of the wick. In some embodiments, the opening of the cylinder is smaller than an outer diameter of the distal portion of the wick. In some embodiments, the cylinder and the heater chassis are formed of different materials from one another. Further, the heater chassis is formed of a material that includes nylon. In some embodiments, the cylinder is formed of a material that includes metal. Further, the material of the cylinder further comprises ceramic. In some embodiments, the inner wall of the heater chassis extends continuously from the lower end to the upper end. Further, the cylinder and the heater chassis are coupled to form a heater arrangement within the housing, and wherein the passage of the heater chassis extends at least 40% of a total height of the heater arrangement.

In some aspects, a volatile material dispenser includes a housing that defines a longitudinal axis and is configured to receive a refill containing a volatile material and a wick. The volatile material dispenser also includes a cylinder that includes an inner wall that defines an opening and an interior edge, a resistor being embedded in the cylinder, and a heater chassis that includes an inner wall that defines a passage between an upper end and a lower end. An interior edge of the cylinder is configured to abut the upper end of the heater chassis. The passage of the heater chassis has a non-uniform diameter that converges toward a diameter of the interior edge of the cylinder.

In some embodiments, the diameter of the passage adjacent to the upper end is substantially equivalent to the diameter defined by the interior edge of the cylinder. In some embodiments, the passage gradually narrows between the upper end and a lower end of the heater chassis. Further, the inner wall of the cylinder and the inner wall of the heater chassis are flush across the interior edge and the upper end. In some embodiments, the passage of the heater chassis is continuous and unobstructed by a protrusion extending inwardly from the inner wall. In some embodiments, the inner wall of the passage and the inner wall of the cylinder are smooth. In some embodiments, the cylinder is formed of at least one of a ceramic material or a metal material. Further, the heater chassis is formed of a nylon material. In some embodiments, the cylinder and the heater chassis are coupled to form a heater arrangement, and, when the refill is received in the housing, a radial gap is formed between the heater arrangement and a distal portion of the wick, the radial gap being non-uniform along the longitudinal axis.

In some aspects, a volatile material dispenser includes a housing that defines a longitudinal axis and is configured to receive a refill containing a volatile material and a wick. The volatile material dispenser also includes a cylinder that includes an inner wall that defines an opening and an interior edge opposite the opening, a resistor being embedded in the cylinder, and a heater chassis that includes an inner wall that defines a passage between an upper end and a lower end. An interior edge of the cylinder is configured to abut the upper end of the heater chassis. In addition, the inner wall of the heater chassis at the upper end defines a substantially flush seam with the inner wall of the cylinder at the interior edge.

In some embodiments, the inner wall of the cylinder defines at least one inflection point. Further, the opening of the cylinder is smaller than a diameter at the interior edge. The diameter at the interior edge is smaller than a diameter of the passage at the lower end of the heater chassis. The passage of the heater chassis converges toward a diameter of the interior edge of the cylinder. In some embodiments, when the wick is received by the housing, a radial gap is defined between the inner wall of the heater chassis and an outer diameter of the wick, and the radial gap is non-uniform between the upper end and the lower end.

In some aspects, a volatile material dispenser includes a housing that defines a longitudinal axis and is configured to receive a refill containing a volatile material and a wick. The volatile material dispenser further includes a heater comprising a resistor and a chassis supporting the heater. The chassis defines a passage about the longitudinal axis, the passage being at least partially defined by an inner wall that is disposed at an oblique angle relative to the longitudinal axis. When the refill is received by the housing, a radial gap is formed within the passage about an outer diameter of a distal portion of the wick. In addition, the radial gap is non-uniform along the longitudinal axis.

In some embodiments, the inner wall of the chassis includes at least one of a curved portion or a tapered portion. Further, the inner wall of the chassis tapers inwardly toward an interior edge of the heater. The passage converges from a lower end of the chassis toward the interior edge of the heater. In some embodiments, a main surface of the heater extends toward a first interior edge that defines an opening, a second interior edge of the heater abuts an upper end of the chassis, and the main surface of the heater is coupled to the chassis. Further, the opening has a diameter that is smaller than a diameter defined by the second interior edge. In some embodiments, the heater comprises less than 50% of a volume of a heater arrangement comprising the heater and the chassis.

In some aspects, a volatile material dispenser includes a housing that defines a longitudinal axis and is configured to receive a refill containing a volatile material and a wick. The volatile material dispenser further includes a heater comprising a resistor and a chassis supporting the heater. The chassis defines a passage about the longitudinal axis, the passage being at least partially defined by an inner wall that is disposed at an oblique angle relative to the longitudinal axis. The inner wall of the chassis defines an innermost point relative to the longitudinal axis and an inner wall of the heater defines an outermost point relative to the longitudinal axis, and wherein the innermost point and the outermost point are disposed a radial distance about the longitudinal axis.

In some embodiments, when the refill is received by the housing, a distal portion of the wick is received within the passage and a radial gap is formed between an outer diameter of the distal portion of the wick and the heater, wherein the radial gap is non-uniform along the longitudinal axis. In some embodiments, when the refill is received by the housing, a distal portion of the wick is received within the passage and a radial gap is formed between an outer diameter of the distal portion of the wick and the chassis, wherein the radial gap is non-uniform along the longitudinal axis. In some embodiments, the heater comprises a ceramic metal composite material and the chassis comprises a nylon material.

DETAILED DESCRIPTION

The present disclosure is directed to heater arrangements for volatile material dispensers that are highly efficient while providing an enhanced plume and avoiding condensation formation within the dispenser. Heater arrangements according to embodiments of the present disclosure generally require less power to dispense a volatile material. For example, dispensers according to embodiments of the present disclosure preferably require 2.0 Watts ("W") or less to perform, whereas existing dispensers sometimes require more than 2.0 W. Further, it has been found that dispensers according to embodiments of the present disclosure generally outperform existing dispensers. More specifically, when operating at comparable power inputs, dispensers according to embodiments of the present disclosure are able to emit more volatile material than existing dispensers. Additionally, dispensers according to embodiments of the present disclosure experience enhanced plume output (i.e., the plume is visibly stronger and more consistent) and reduce condensation formation therein. While the present disclosure may be embodied in many different forms, the present disclosure is to be considered only as an exemplification of the principles of the disclosure, and it is not intended to limit the disclosure to the embodiments illustrated.

Figure 1:
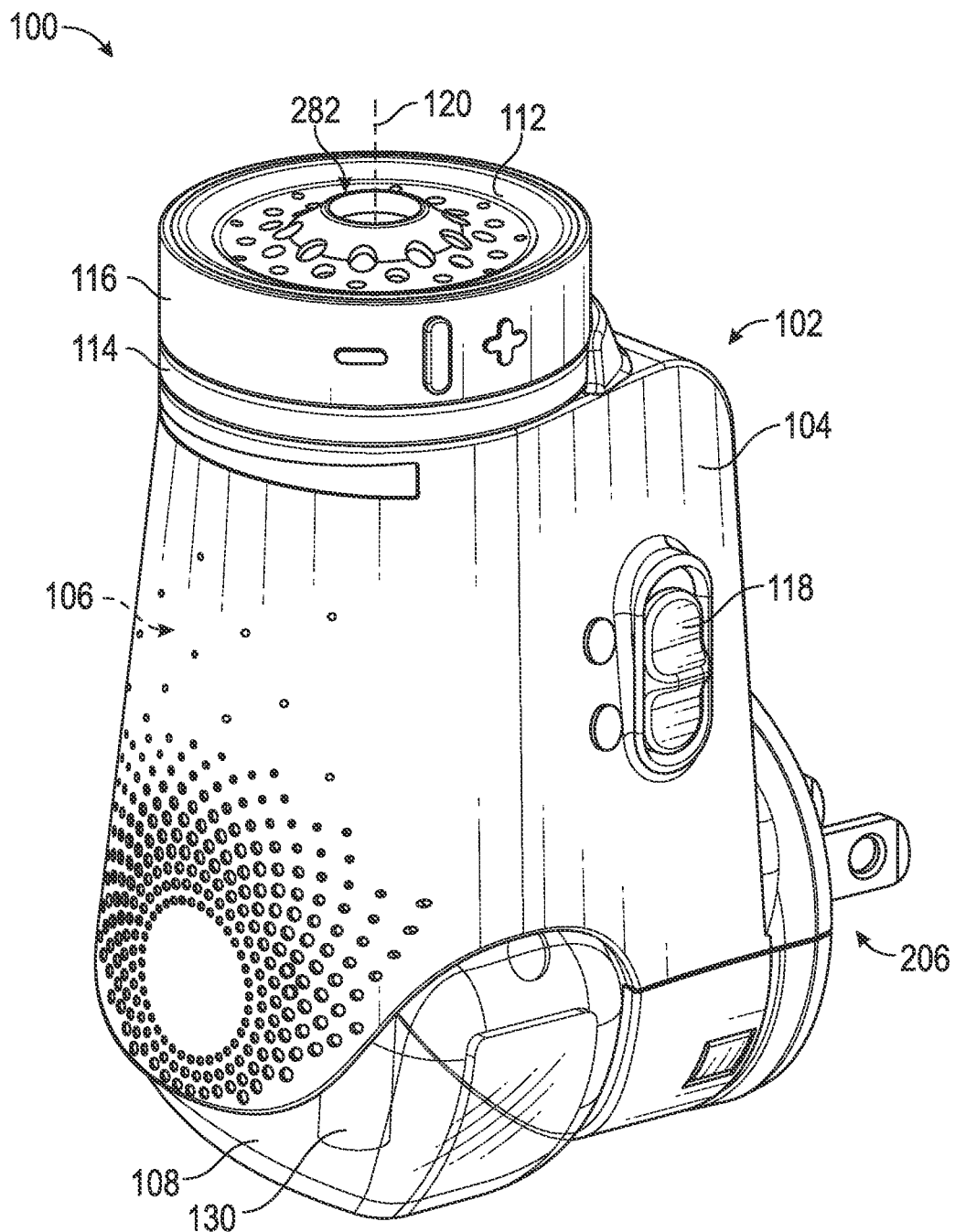
FIG. 1 is a front isometric view of a dispensing system including a dispenser and a refill according to an embodiment of the present disclosure.
Figure 2:
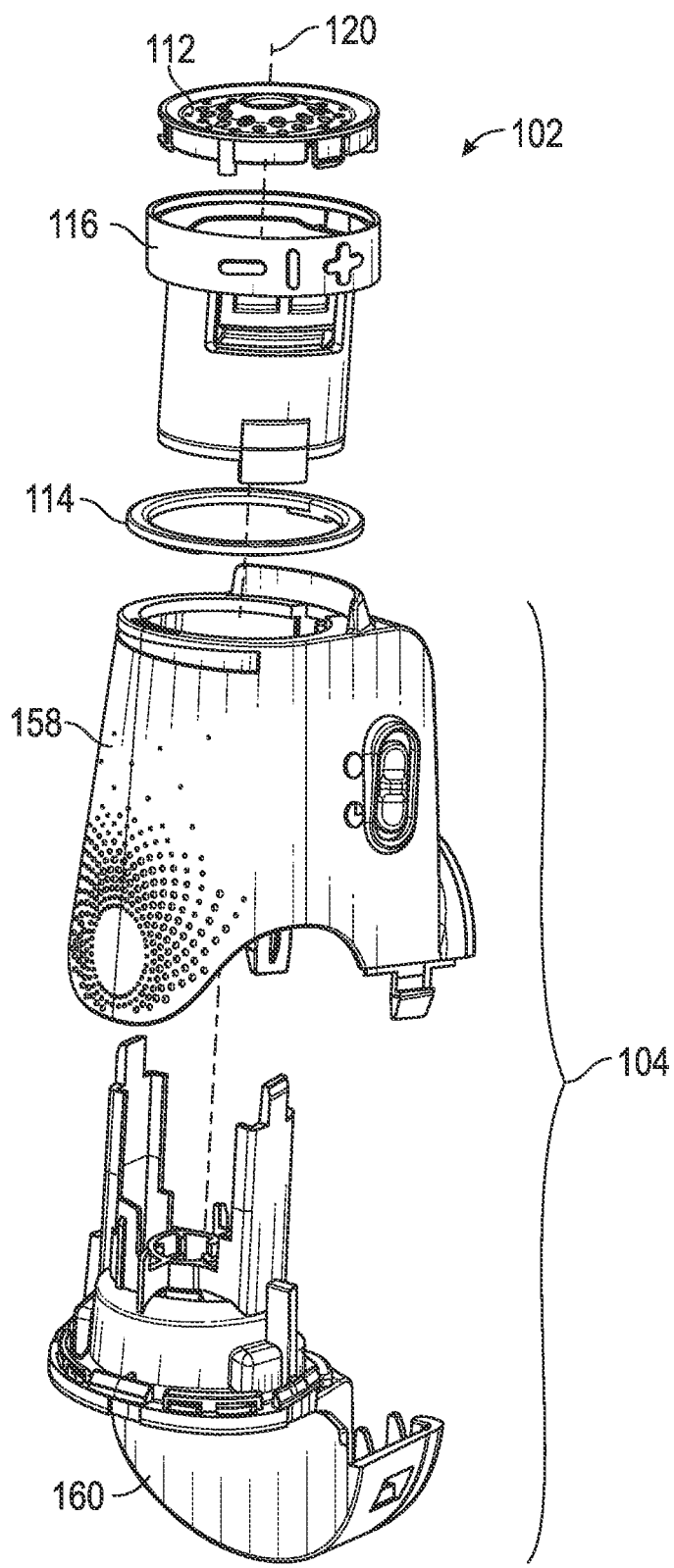
FIG. 2 is a front isometric exploded view of the dispenser of FIG. 1.

The dispensers described herein may be used as plug-in devices, which are configured to be inserted into an outlet to be powered. Alternatively, aspects disclosed herein may be used in alternative dispensers, such as dispensers that are stand-alone devices or hand-held devices powered by a battery. FIGS. 1-29 illustrate one particular embodiment of a dispensing system 100 according to the present disclosure. Referring to FIG. 1, the dispensing system 100 comprises a dispenser 102 that generally includes a housing 104 having an internal cavity 106 for accepting a volatile material refill 108 and a heater arrangement 110 (see, e.g., FIG. 13). The volatile material refill 108 may be similar in structure and function to the refill disclosed in U.S. Pat. Pub. 2019/0091365 filed on Jul. 25, 2018, the disclosure of which is incorporated by reference in its entirety. The dispenser 102 further includes a top cover 112, a visual indicator 114, and a control dial 116. Each of the top cover 112, the control dial 116, the visual indicator 114, and the housing 104 are configured to be assembled together as shown by an exploded view of FIG. 2. When assembled, the dispenser 102 defines a longitudinal axis 120. The housing 104, the top cover 112, the visual indicator 114, and the control dial 116 may be similar in structure and function to the housing, the top cover, the visual indicator, and the control dial disclosed in a U.S. patent application entitled "Dispenser with a Visual Indication System," which was filed on the same day by the same assignee as the present disclosure and is incorporated herein by reference in its entirety.

Figure 3:
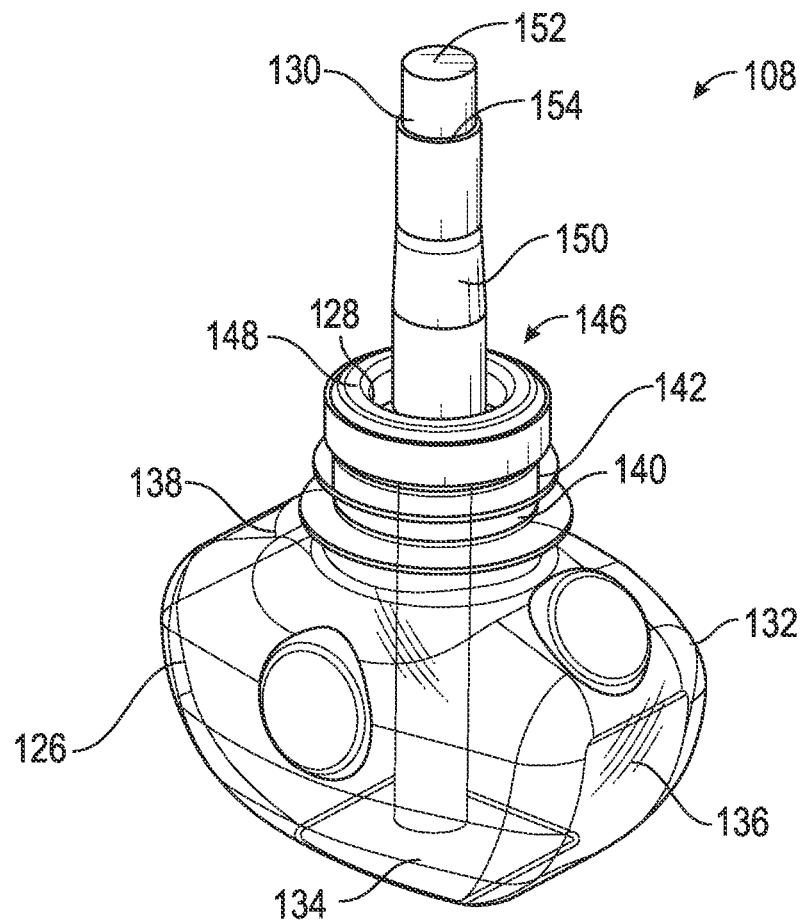
FIG. 3 is a front isometric view of the refill of FIG. 1.

Referring to FIG. 3, the refill 108 includes a container 126 with a volatile material therein (not shown), wherein the container 126 is adapted to be retained by the housing 104 of the dispenser 102 (see, e.g., FIG. 1). The container 126 includes a retaining mechanism 128 to hold a wick 130 within the container 126 and a body 132 with the volatile material disposed therein. The body 132 includes a base portion 134 and a sidewall 136 that extends upwardly toward a top portion 138. In one instance, the sidewall 136 may be generally cylindrical or rectangular, although other sidewall configurations are possible. The top portion 138 also may be integral with a neck 140. The neck 140 includes a threaded portion 142 disposed on an outer surface thereof and a refill opening 146 disposed through a top portion 148 thereof, wherein the refill opening 146 allows access to the volatile material. The retaining mechanism 128 is disposed within the neck 140 and further includes a sheath 150 that extends around at least a portion of the wick 130 to protect the wick 130. In the present embodiment, an upper, free end 152 of the wick 130 extends above a distal edge 154 of the sheath 150.

Returning to FIG. 1, although a specific dispenser and container are described with particularity, it is contemplated that the heater arrangements disclosed herein may be utilized in conjunction with any type of refill and/or container. For example, useful refills include, but are not limited to, the containers described in U.S. Pat. No. 7,032,831, and the containers described in U.S. Pat. Pub. 2011/0139885, both of which are owned by the same assignee as the present disclosure and incorporated herein by reference in their entirety. Further, it is contemplated that the heater arrangement disclosed herein may be used in conjunction with other dispenser arrangements, such as the fan arrangement described in U.S. Pat. App. No. 2018/0103507 filed on Oct. 7, 2016, which is also owned by the same assignee as the present disclosure and incorporated herein by reference in its entirety.

The volatile material disposed in the container 126 may be any type of volatile material adapted to be dispensed into an environment. For example, the container 126 may include a cleaner, an insecticide, an insect repellant, an insect attractant, a disinfectant, a mold or mildew inhibitor, a fragrance, a disinfectant, an air purifier, an aromatherapy scent, an antiseptic, an odor eliminator, a positive fragrancing volatile material, an air-freshener, a deodorizer, or the like, and combinations thereof. Additives may be included in the volatile material, such as, for example, fragrances, preservatives, sanitizers, mold or mildew inhibitors, or the like, and combinations thereof. For example, the fluid may comprise OUST®, an air and carpet sanitizer for household, commercial, and institutional use, or GLADE®, a household deodorant, both sold by S. C. Johnson and Son, Inc., of Racine, Wisconsin. The volatile material additionally or alternatively comprises any fluid known to those skilled in the art that can be dispensed from a container. The container 126 is therefore adapted to dispense any number of different fluid formulations.

Figure 4:
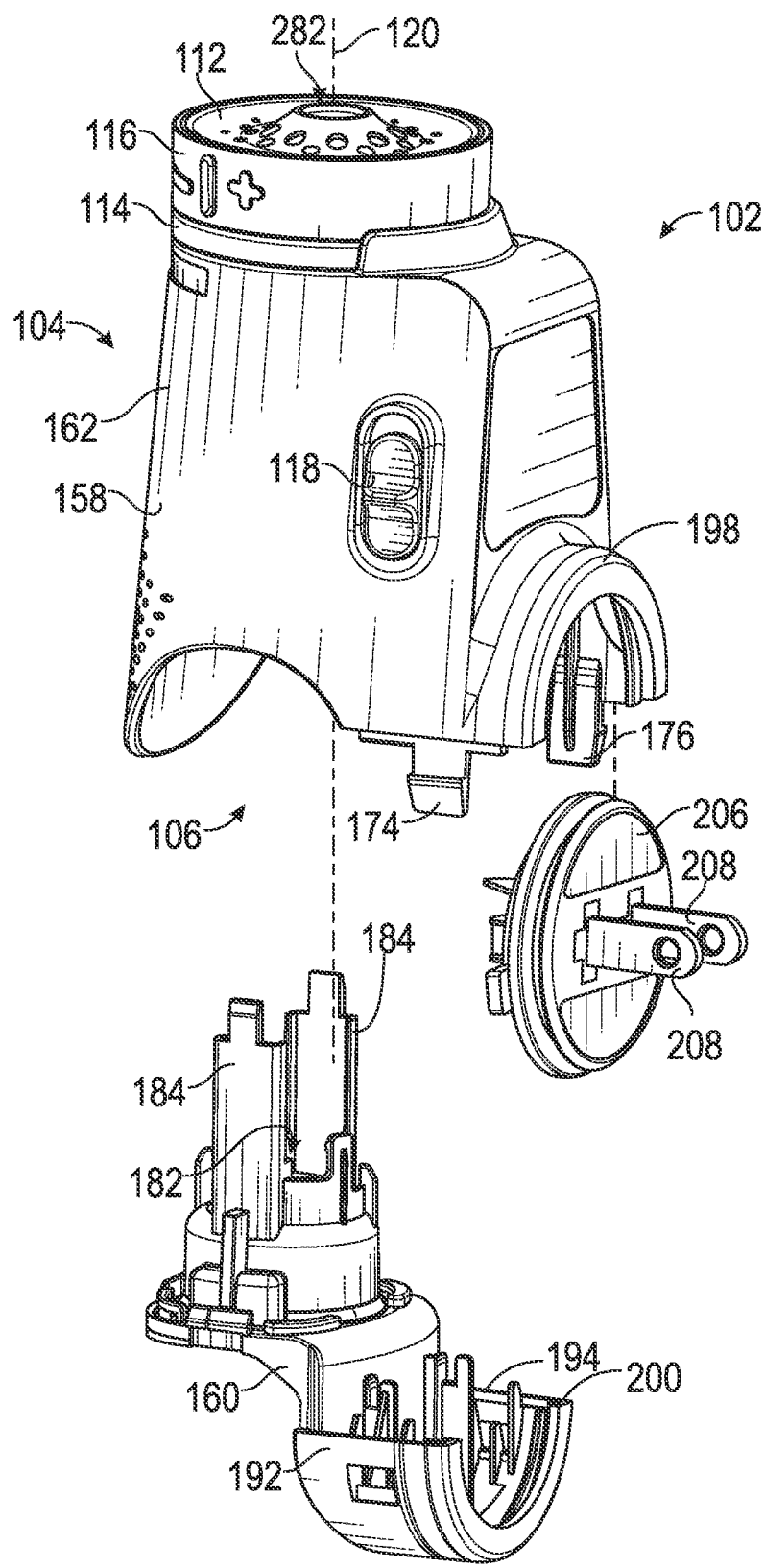
FIG. 4 is a rear isometric exploded view of the dispenser of FIG. 1 including an upper casing and a lower casing.
Figure 5:
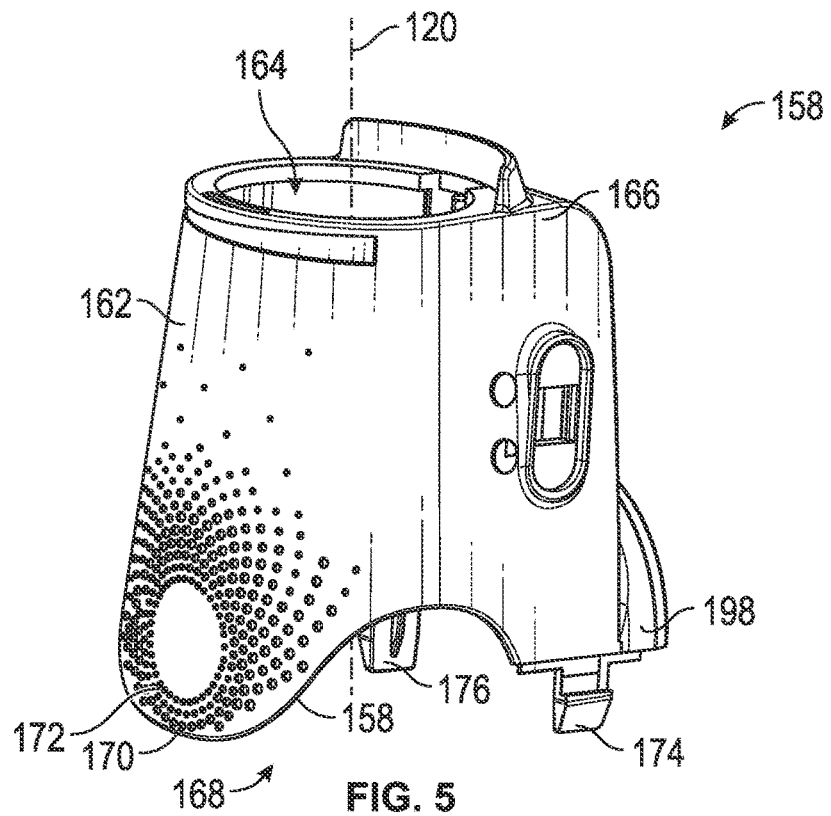
FIG. 5 is a front isometric view of the upper casing of FIG. 4.
Figure 6:
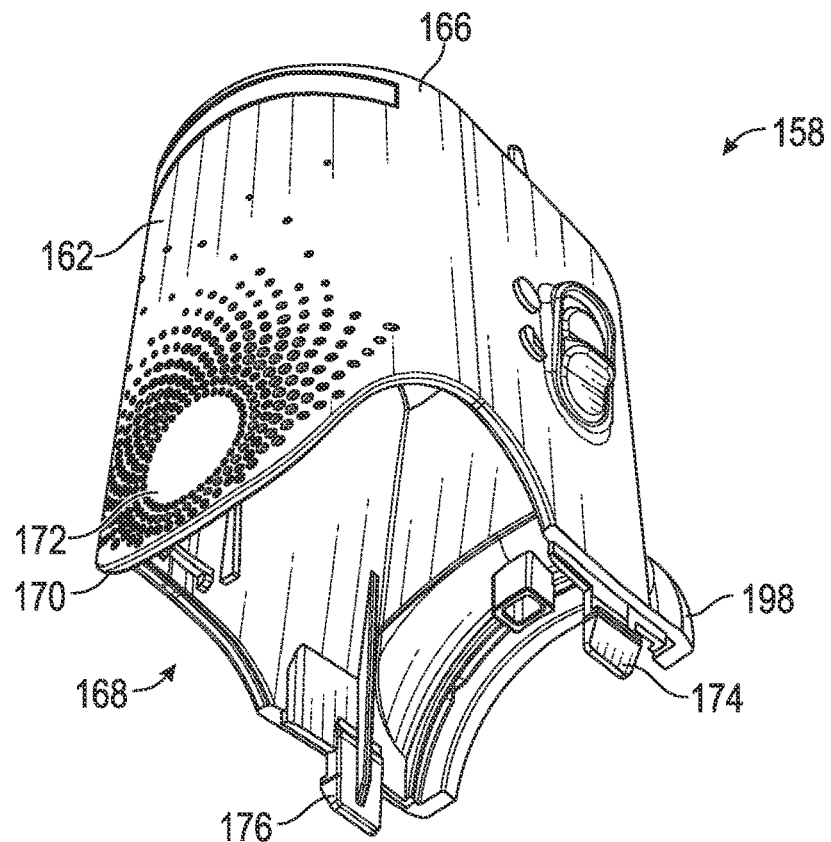
FIG. 6 is another front isometric view of the upper casing of FIG. 4.

Now turning to FIG. 4, the housing 104 generally includes an upper casing 158 and a lower casing 160 configured to be attached to each another to define the internal cavity 106. The upper casing 158 and the lower casing 160 comprise a thin walled material and may be formed using methods known in the art, such as thermoforming or injection molding. Referring particularly to FIG. 5, the upper casing 158 comprises an upper tubular wall 162 defining a circular receiving aperture 164 disposed at a first upper end 166 thereof. The upper tubular wall 162 further defines an upper cavity 168 that extends from the circular receiving aperture 164 to a lower edge 170 disposed at a second upper end 172 thereof. A first latch 174 and a second latch 176 extend substantially perpendicularly from the lower edge 170 and are substantially coplanar with portions of the upper tubular wall 162.

Figure 7:
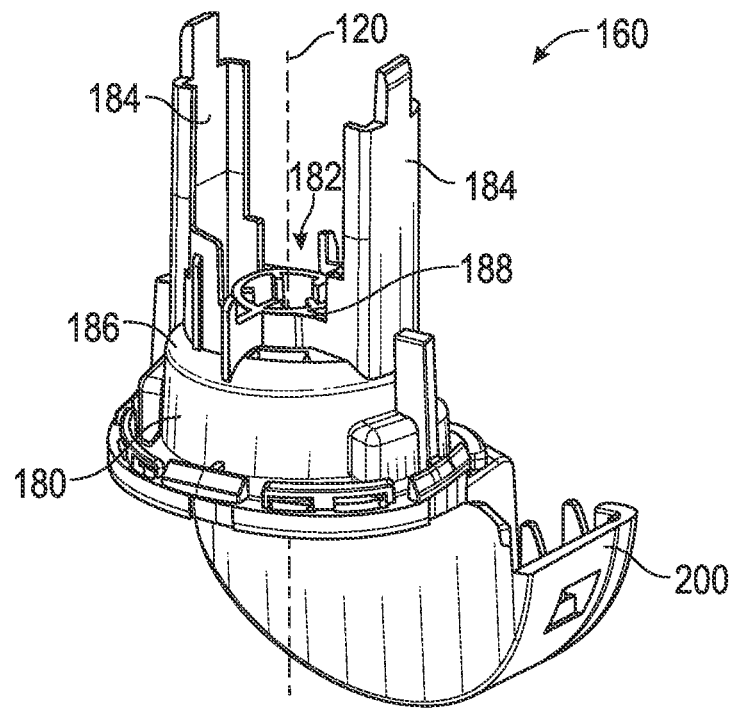
FIG. 7 is a front isometric view of the lower casing of FIG. 4.
Figure 8:
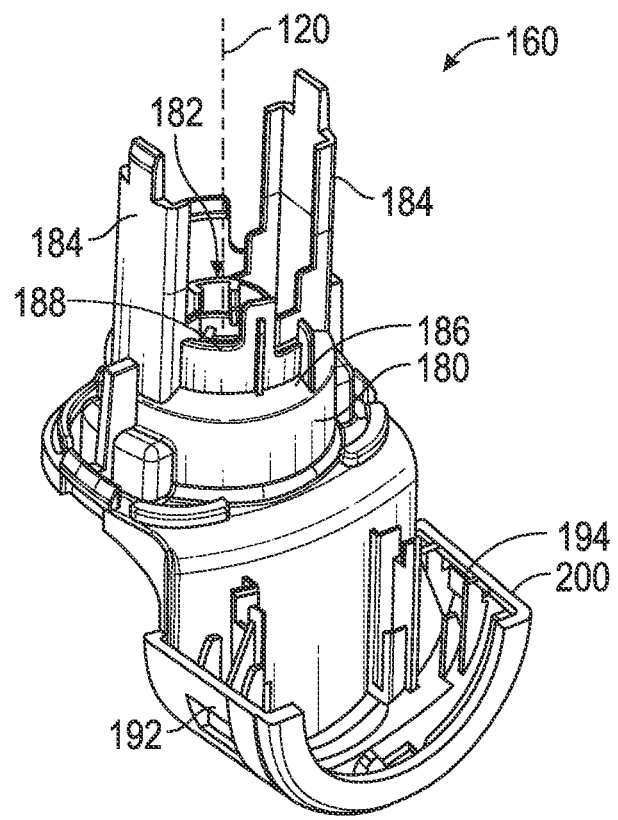
FIG. 8 is a rear isometric view of the lower casing of FIG. 4.

Turning to FIGS. 7 and 8, the lower casing 160 comprises a cylindrical center portion 180 that defines a channel 182 therethrough. Two elongate guide posts 184 extend upwardly from a first lower end 186 of the lower casing 160 and are generally parallel to the longitudinal axis 120. The elongate guide posts 184 extend from the first lower end 186 on opposing sides of a first channel end 188 of the channel 182 and are provided to secure the heater arrangement 110 (see, e.g., FIG. 12) therein, which will be described in greater detail below.

Figure 9:
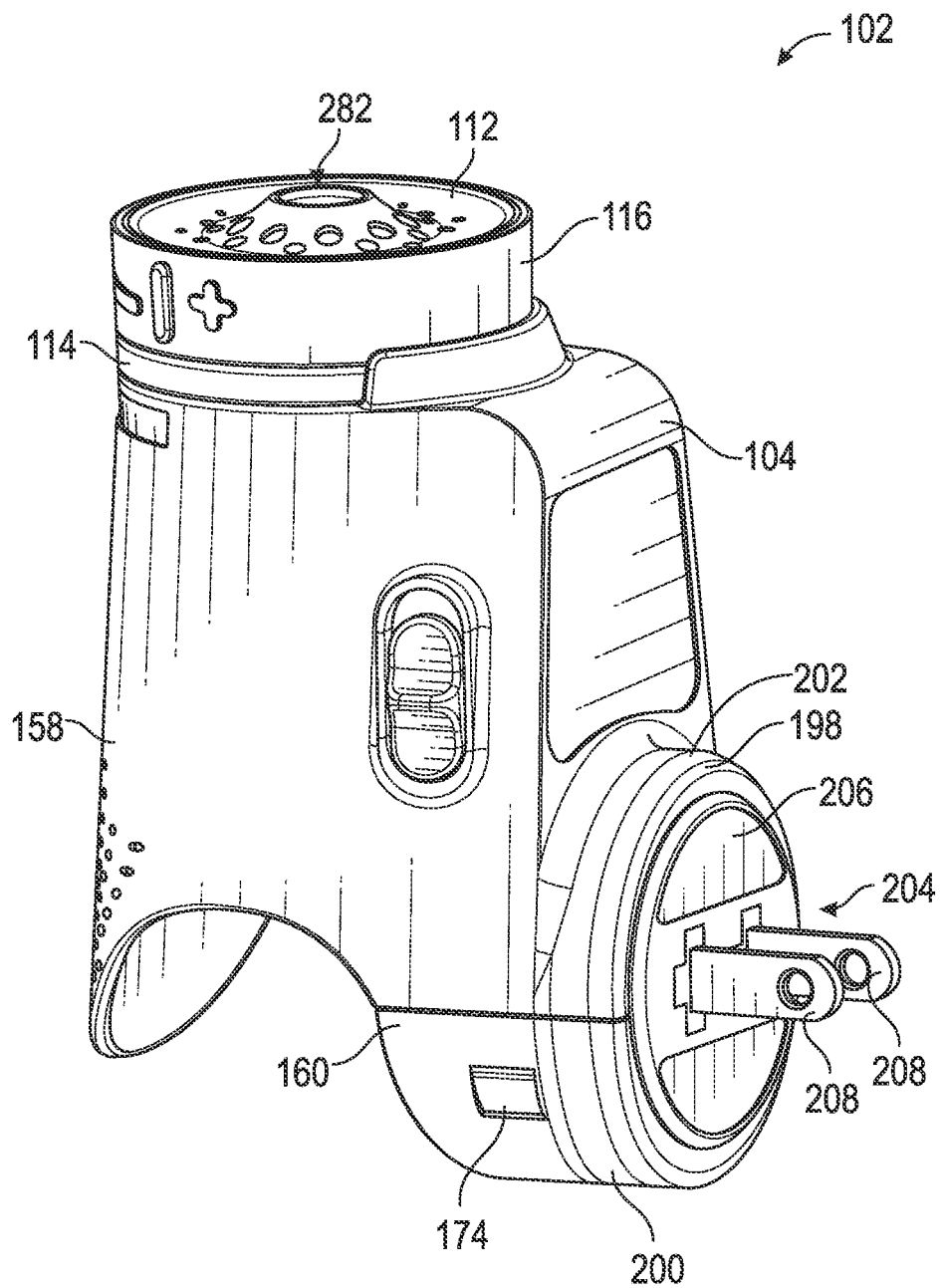
FIG. 9 is a rear isometric view of the dispenser of FIG. 1.

Returning to FIG. 4, the upper casing 158 and the lower casing 160 are configured to attach to each other. More specifically, the upper casing 158 is configured to receive the elongate guide posts 184 of the lower casing 160, and the first latch 174 and the second latch 176 of the upper casing 158 are configured to secure to a first latch receiving structure 192 and a second latch receiving structure 194 of the lower casing 160, respectively. Further, as best seen in FIG. 9, a first hemi-cylindrical extension 198 of the upper casing 158 and a second hemi-cylindrical extension 200 of the lower casing 160 connect to create a cylindrical extension 202, which defines a cylindrical receiving chamber 204 that is configured to receive and retain a plug assembly 206 therein. The plug assembly 206 may extend from the cylindrical receiving chamber 204 defined by the upper casing 158 and the lower casing 160 of the housing 104. The plug assembly 206 may include two electrical prongs 208 adapted for insertion into a conventional outlet. While the plug assembly 206 is shown as being a conventional plug assembly for the United States, a plug assembly adapted for use in any other country may be utilized. In addition, the plug assembly 206 may include any features known in the art, for example, the plug assembly 206 may be partially or fully rotatable, similar to the plug assemblies disclosed in U.S. Pat. No. 8,821,171 filed on Sep. 22, 2011, and U.S. Pat. No. 8,858,236 filed on Oct. 28, 2011, the disclosures of which are incorporated by reference in their entirety.

Figure 10:
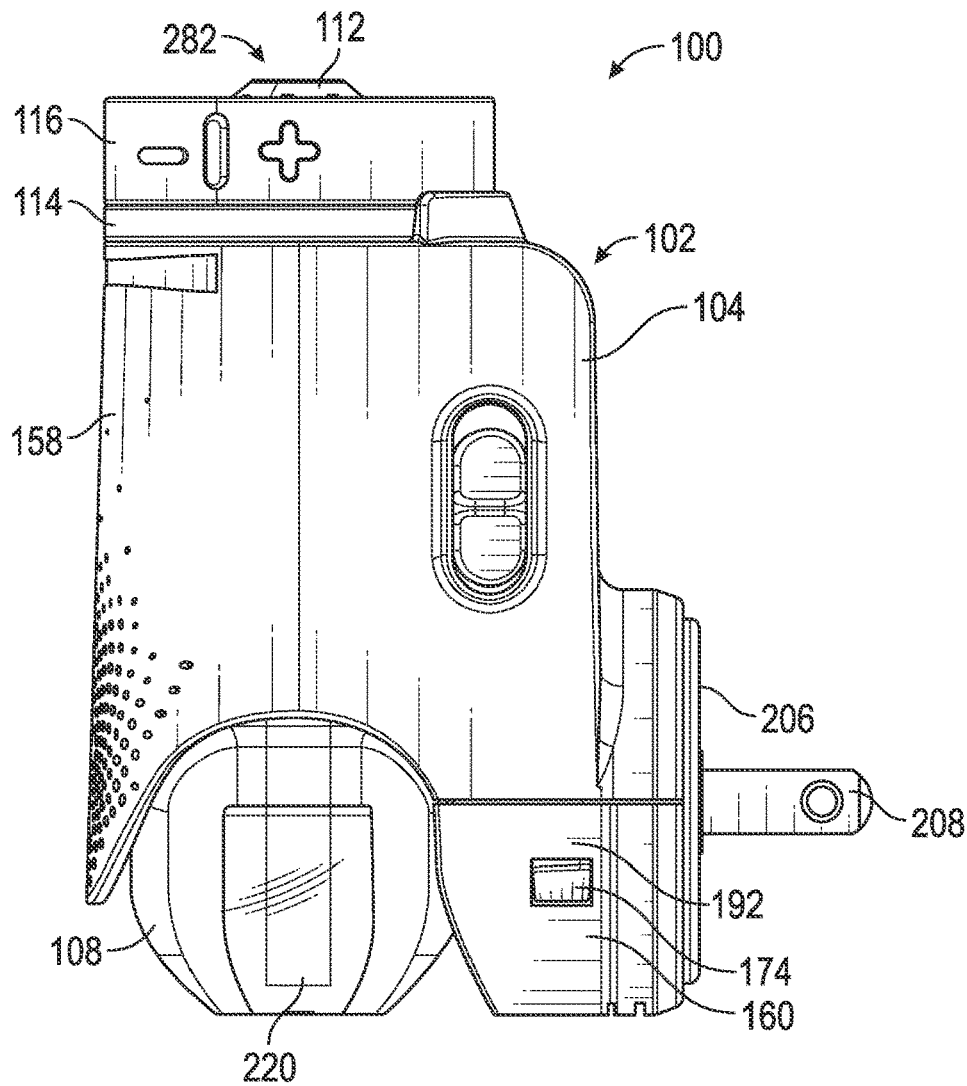
FIG. 10 is a left side elevational view of the dispensing system of FIG. 1.
Figure 11:
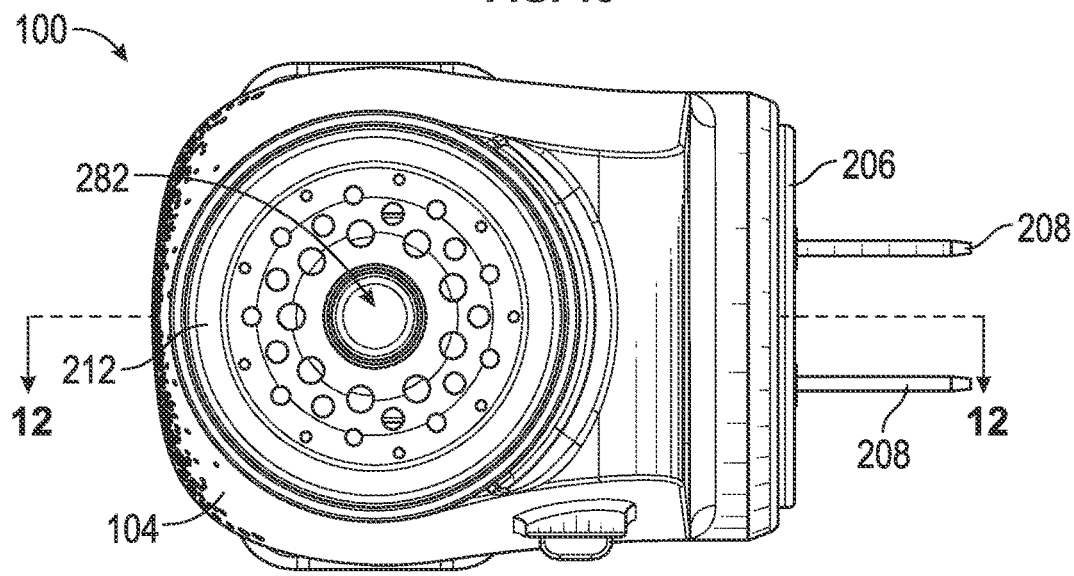
FIG. 11 is a top plan view of the dispensing system of FIG. 1.
Figure 12:
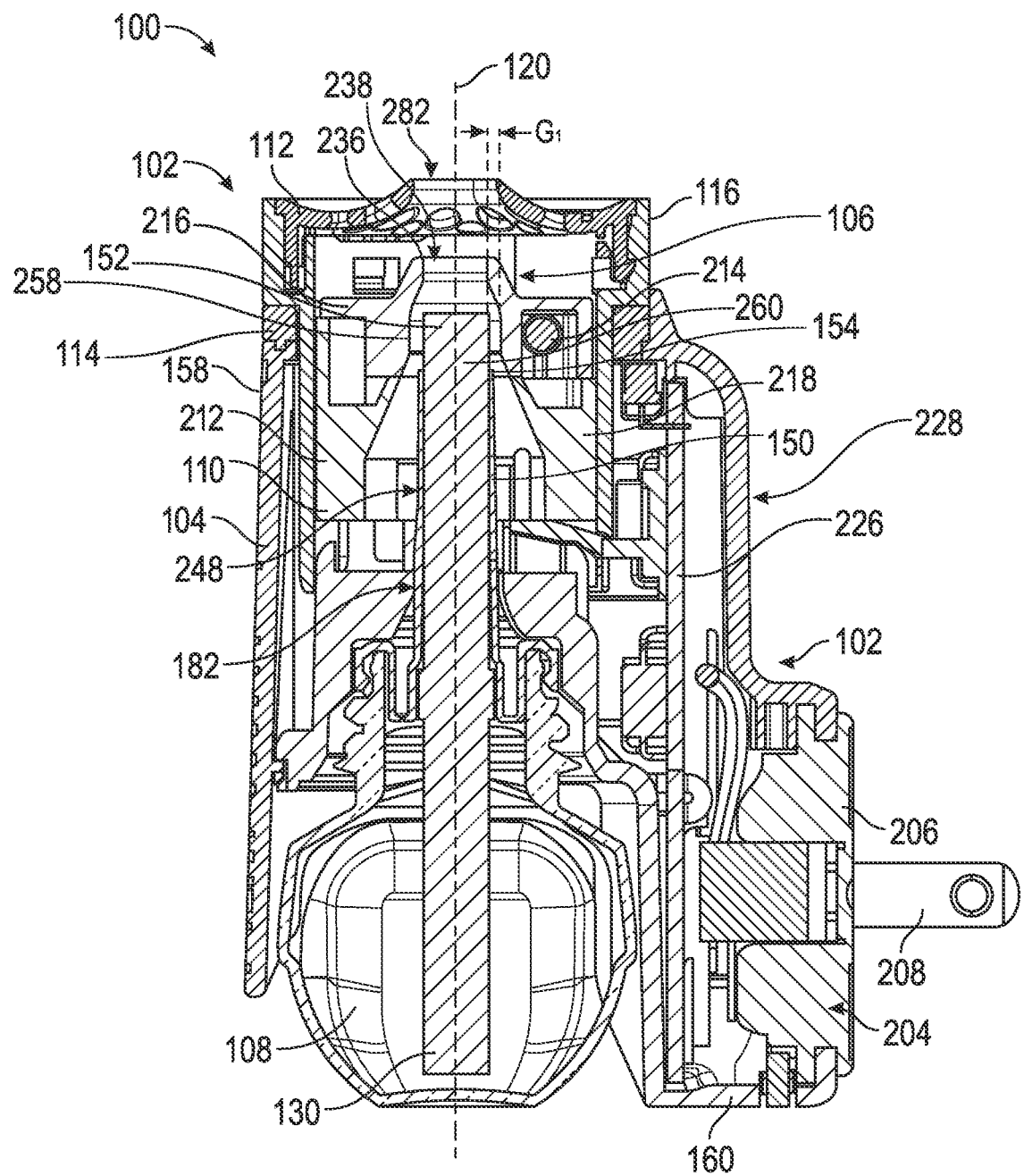
FIG. 12 is a cross-sectional view of the dispensing system of FIG. 11 taken across line 12-12 of FIG. 11.
Figure 13:
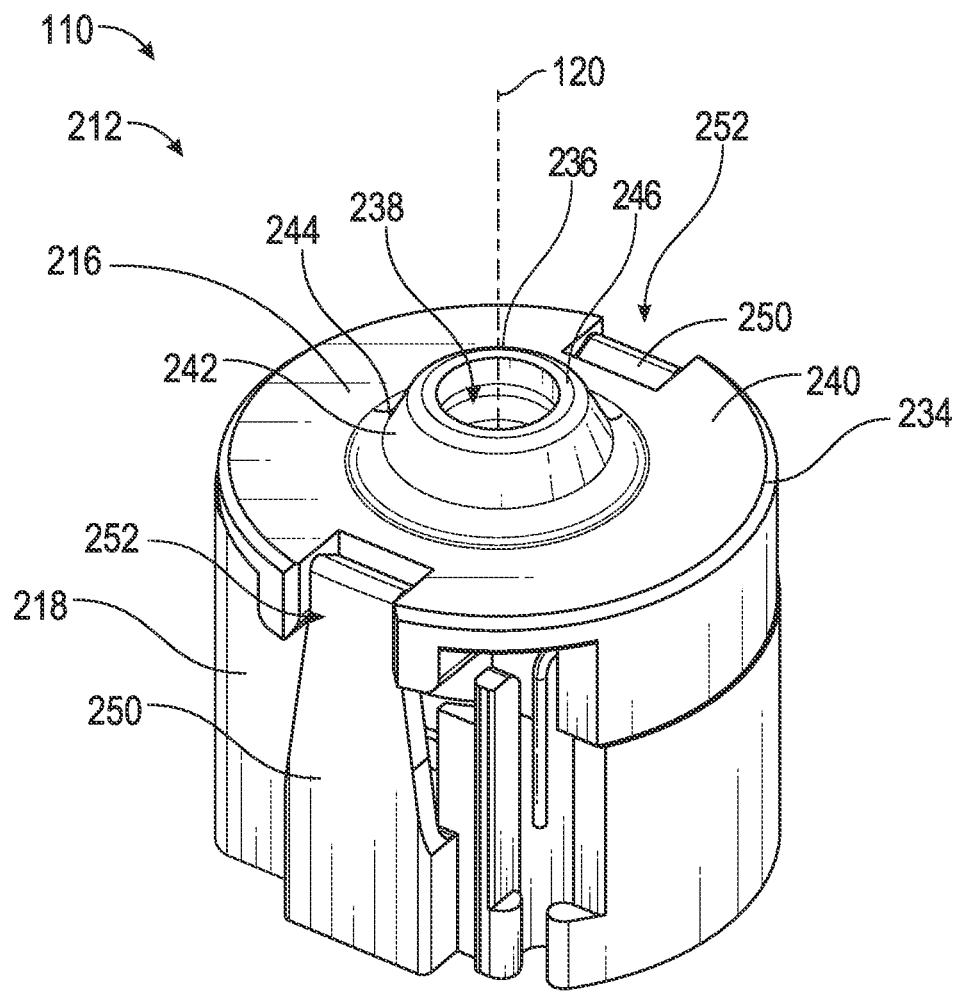
FIG. 13 is a front isometric view of a heater arrangement according to an embodiment of the present disclosure.

FIGS. 10 and 11 provide a side elevational view and a top plan view of the dispensing system 100, respectively. FIG. 12 illustrates a cross-sectional view of the dispensing system 100 taken across line 12-12 of FIG. 11. Referring particularly to FIG. 12, the channel 182 of the lower casing 160 is configured to receive the wick 130 of the refill 108. That is, the refill 108 may be inserted into the housing 104 by inserting the wick 130 upwardly through the channel 182 of the lower casing 160 toward the internal cavity 106 of the housing 104 along a direction defined by the longitudinal axis 120, the axis preferably being substantially vertical when the dispenser 102 is in use. Further, the heater arrangement 110 is disposed within the internal cavity 106 so that it is supported by the lower casing 160.

Figure 14:
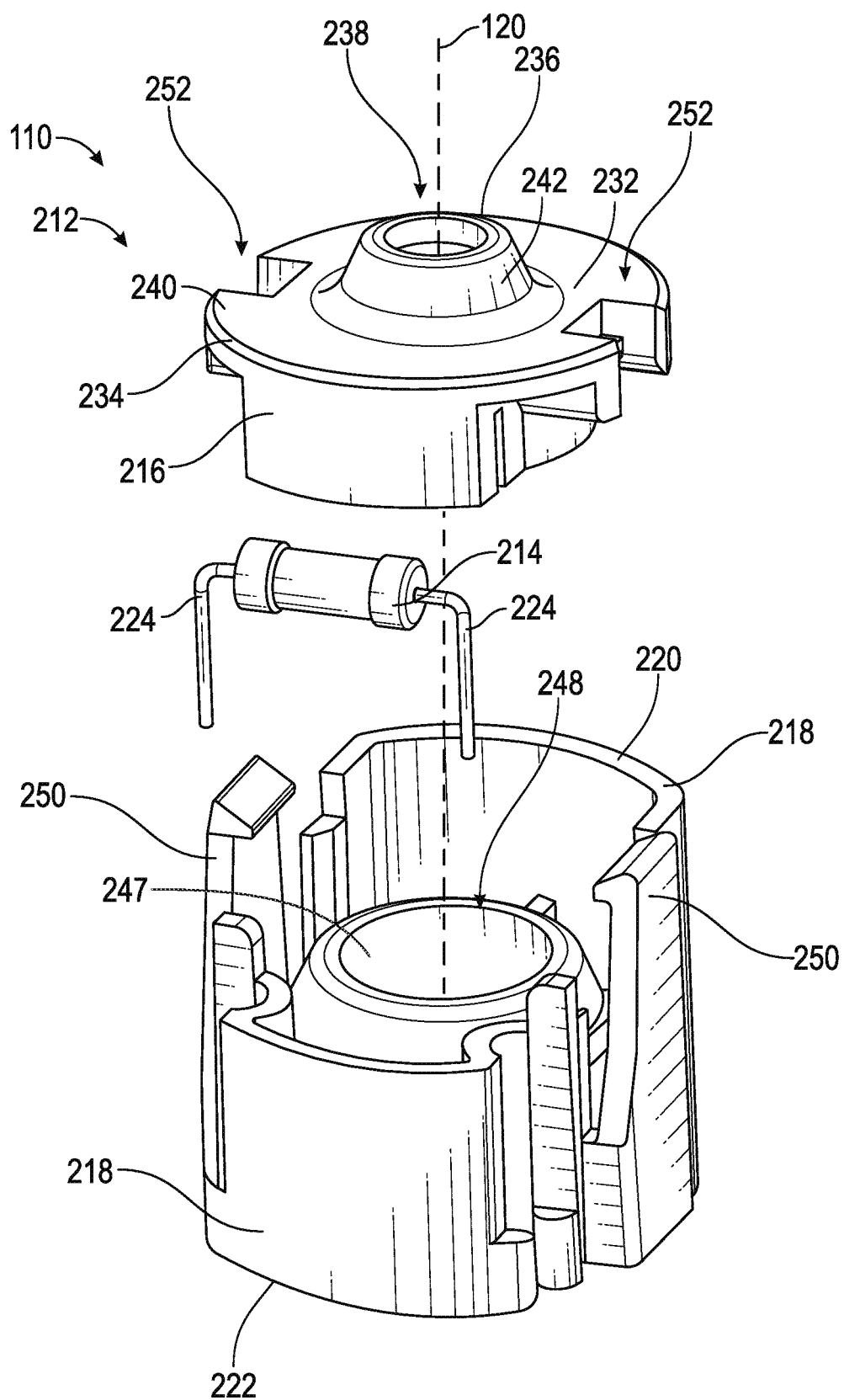
FIG. 14 is an exploded view of the heater arrangement of FIG. 13.

Turning to FIGS. 13-17, the heater arrangement 110 generally uses a heating element to provide heat to the wick 130, which ultimately works to turn a volatile material (e.g., a fragrance oil) into a vapor or gas. Particularly, as best seen in FIG. 14, the heater arrangement 110 uses a heating element 212 comprising a resistor 214 that is potted, embedded, or otherwise disposed within a cylinder 216. The cylinder 216 is configured to be supported by a heater chassis 218 having an upper end 220 and a lower end 222. More specifically, when the heater arrangement 110 is assembled, the cylinder 216 is configured to abut the upper end 220 of the heater chassis 218. The heater chassis 218 is preferably made of a material having good radiation resistance properties, such as, e.g., a high temperature nylon. Preferably, the cylinder 216 is made of a highly thermally conductive material, such as, e.g., a ceramic metal composite having a high metal content (e.g., aluminum). Incorporating a ceramic metal composite having high amounts of metal results in enhanced heat transfer across the cylinder 216. Additionally or alternatively, the cylinder 216 and/or any potting disposed within the cylinder 216 may comprise other types of thermally conductive material. Further, in some embodiments, the cylinder 216 may comprise a resistive metal oxide coating that is deposited by sputter coating or spray coating thereon, or, it may comprise no coating thereon. Additionally, in some embodiments, the cylinder 216 may be coated with a metal oxide coating having a precise resistance value to create a desired resistance value for the heater arrangement 110.

Figure 15:
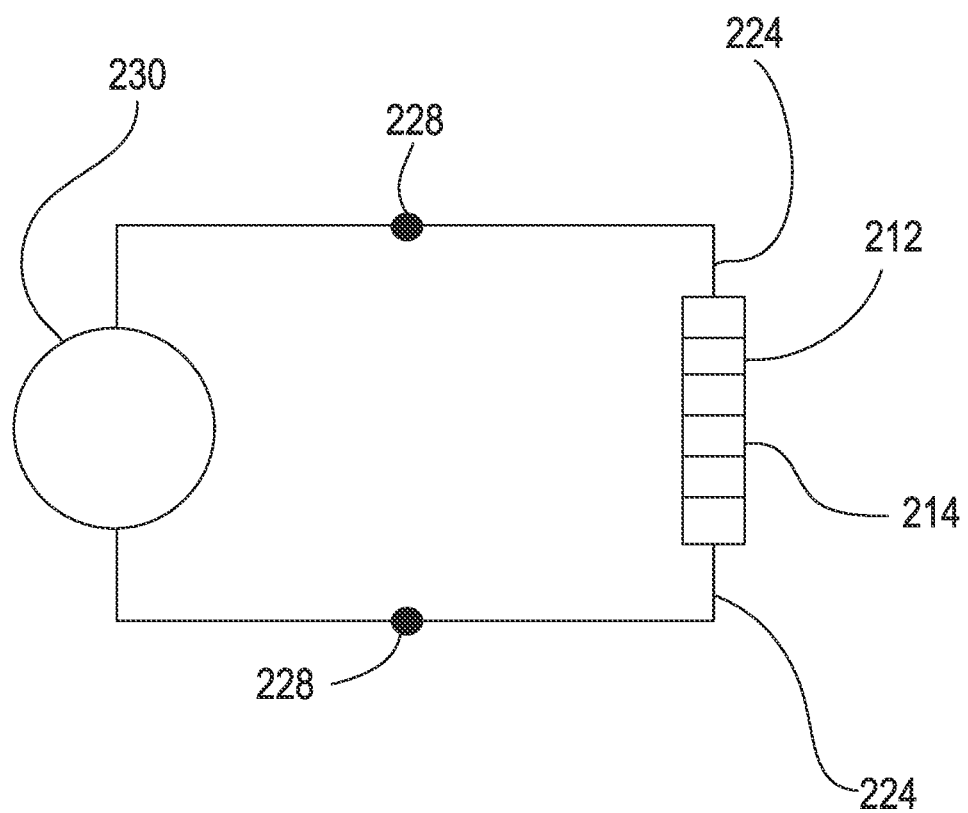
FIG. 15 is an electrical schematic of the heater arrangement of FIG. 13.
Figure 16:
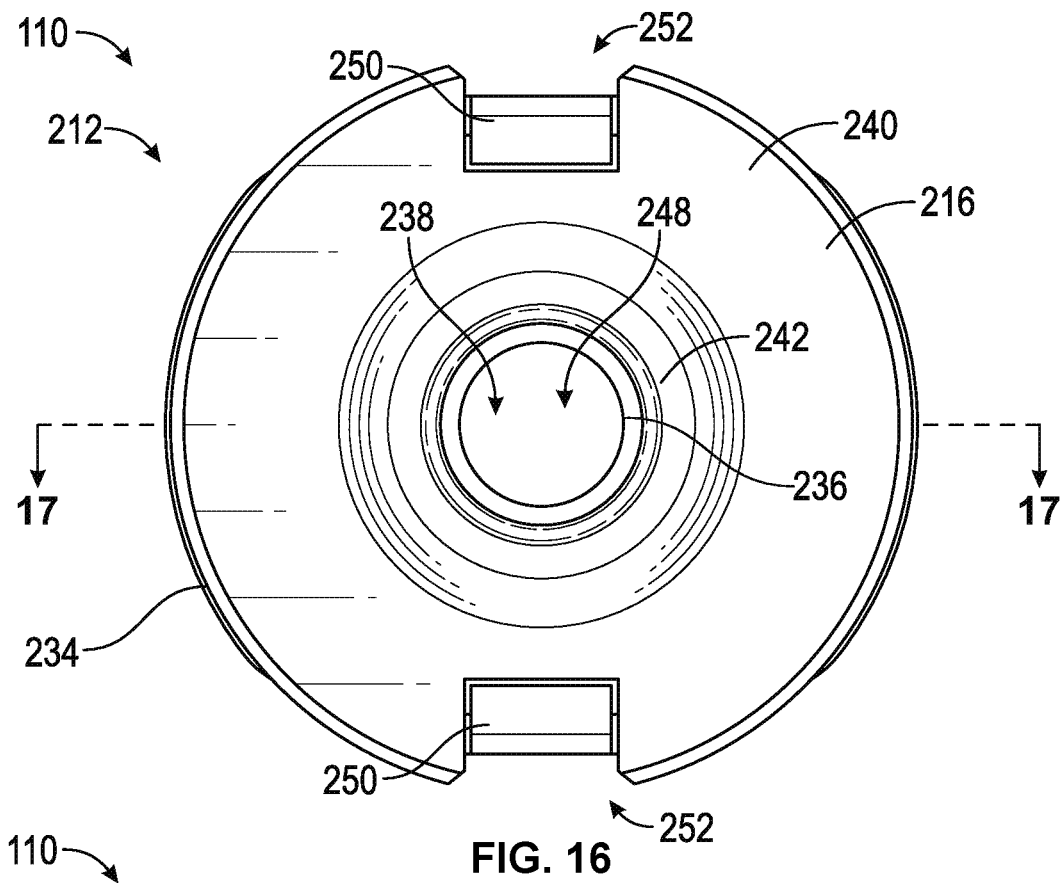
FIG. 16 is a top plan view of the heater arrangement of FIG. 13.

One or more connectors 224 are integral with or connected to ends of the resistor 214. As best seen in FIG. 15, the one or more connectors 224 extend away from the resistor 214 and terminate in terminals 228. Either the connector(s) 224 or terminals 228 may connect to a power supply, circuit board, and/or other electrical components of the dispensing system 100. In the illustrated embodiment, the connectors 224 extend from the heating element 212 (the resistor 214 in the present embodiment) to a power supply 230 (e.g., the plug assembly 206 shown in FIG. 9).

Figure 17:
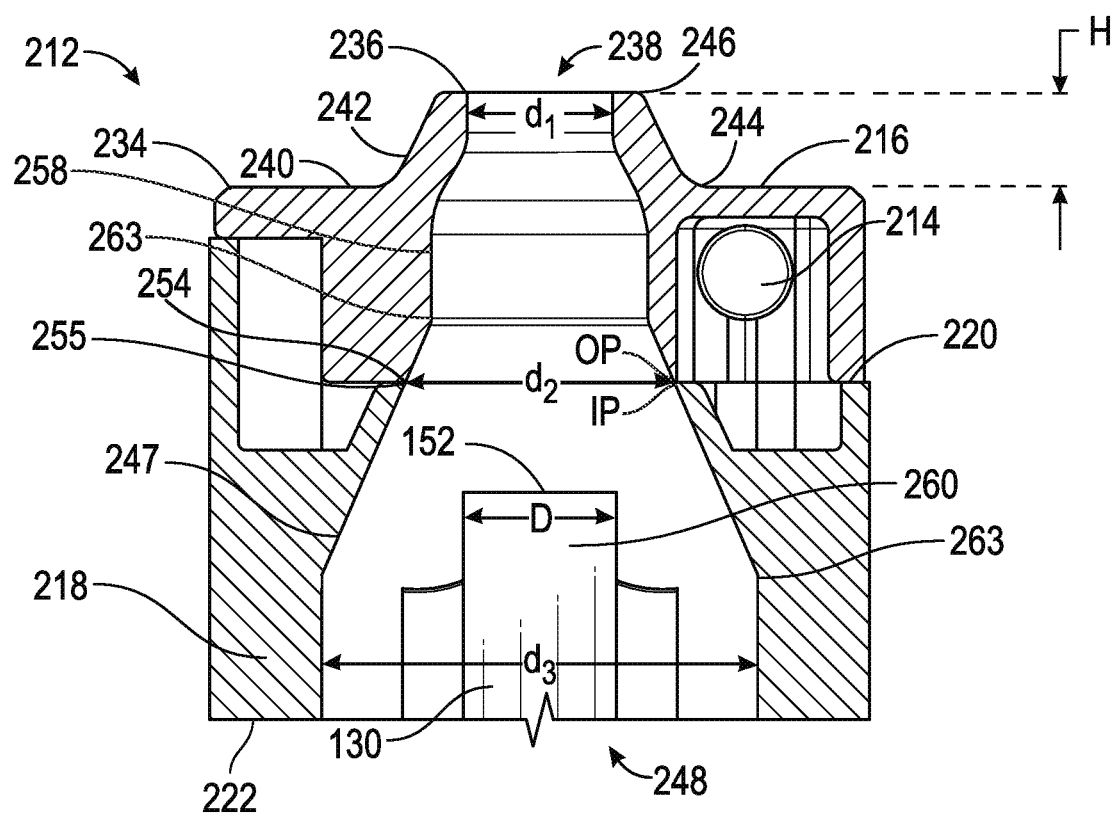
FIG. 17 is a cross-sectional view of the heater arrangement of FIG. 16 taken across line 17-17 of FIG. 16.
Figure 18:
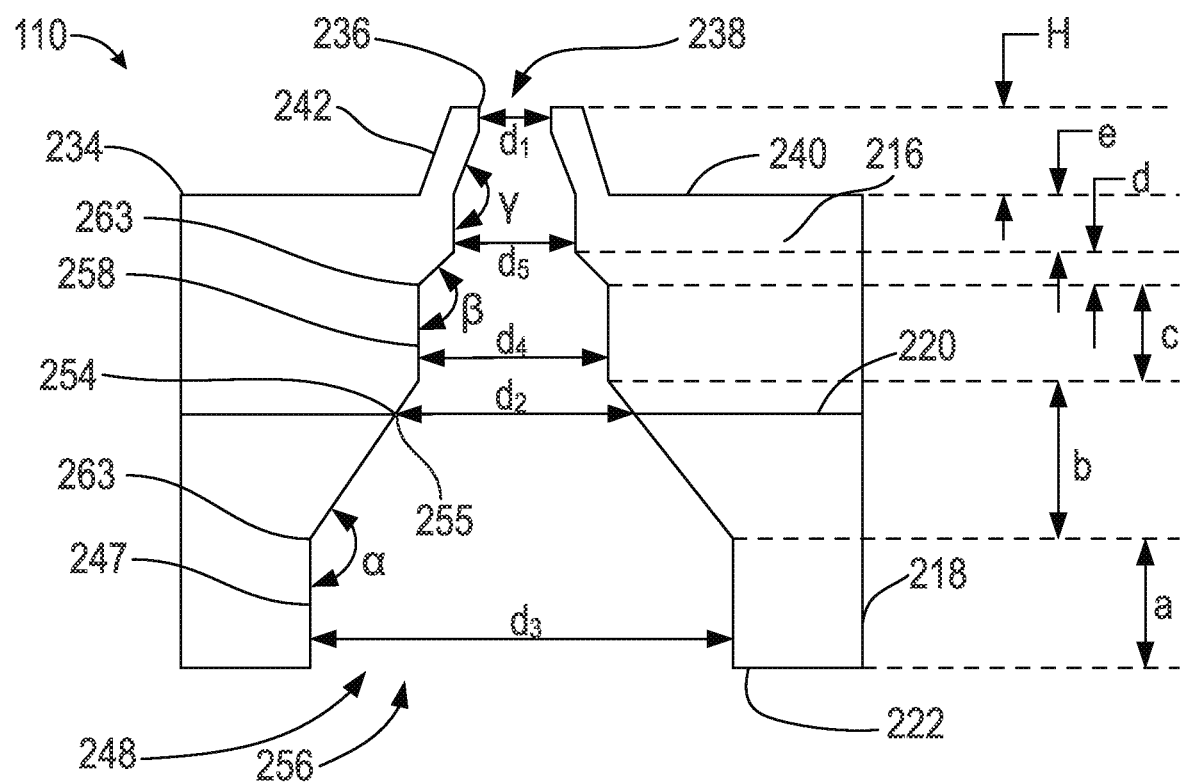
FIG. 18 is a schematic of a heater arrangement according to an embodiment of the present disclosure.
Figure 19:
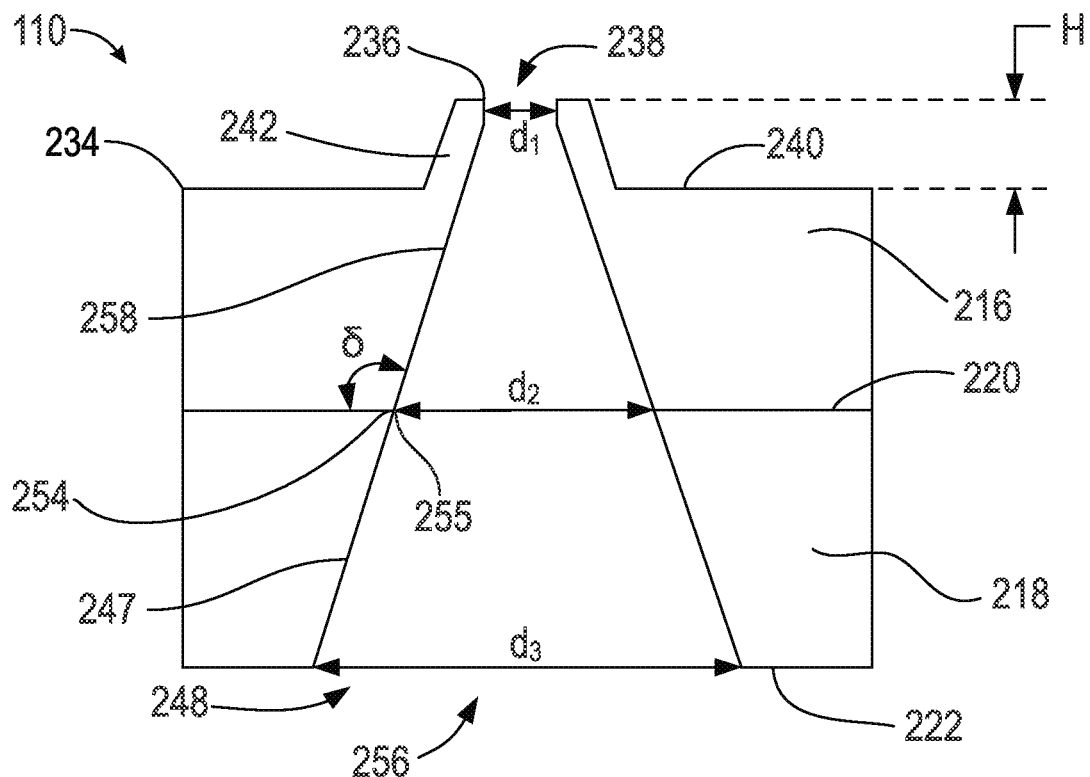
FIG. 19 is a schematic of a heater arrangement according to another embodiment of the present disclosure.

Returning to FIG. 14, the cylinder 216 generally comprises an annular body 232 having a peripheral edge 234, a first interior edge 236 defining an opening 238, and a main surface 240 extending therebetween. As best seen in FIG. 17, which is a cross-sectional view of the heater arrangement 110 taken across line 17-17 of FIG. 16, the peripheral edge 234 and the first interior edge 236 are disposed on different planes. That is, the first interior edge 236 is elevated relative to the peripheral edge 234 and the main surface 240 by a height H. Preferably, the height H is between approximately 1 millimeter ("mm") and 10 mm. In some embodiments, the height H may be less than 5 mm. In some embodiments, the height H may be less than 3 mm.

Still referring to FIG. 17, the main surface 240 extends radially inward from the peripheral edge 234 toward the first interior edge 236 and a heater chimney 242, which curves away from the main surface 240 to the first interior edge 236. Accordingly, the heater chimney 242 and the first interior edge 236 are elevated relative to the main surface 240 and the peripheral edge 234 of the cylinder 216. Further, the heater chimney 242 gradually restricts from a first end 244 proximate the main surface 240 to a second end 246 distal of the main surface 240. The main surface 240 extends substantially planar from the peripheral edge 234 until it reaches the first end 244 of the heater chimney 242. The heater chimney 242 gradually curves until it reaches the first interior edge 236 and the second end 246. Thus, the main surface 240 extends from the peripheral edge 234 so that it is planar for at least 50% of a radial distance between the peripheral edge 234 and the first interior edge 236. In some embodiments, the main surface 240 may extend planar for more than 60% of the radial distance between the peripheral edge 234 and the first interior edge 236. However, in some embodiments, the main surface 240 may extend planar for less than 50% of the radial distance between the peripheral edge 234 and the first interior edge 236.

Returning to FIG. 14, the heater chassis 218 includes an inner wall 247 that defines a passage 248 therethrough that extends from the upper end 220 to the lower end 222 and is configured to receive the wick 130 (see, e.g., FIG. 12) therein, as will be described in greater detail below. Further, the heater chassis 218 is configured to couple to the cylinder 216 using latches 250 extending substantially parallel to the axis 120 that is axially aligned with the passage 248. The latches 250 are configured to abut latch receiving portions 252 of the cylinder 216. Accordingly, when assembled, the opening 238 of the cylinder 216 and the passage 248 of the heater chassis 218 are configured to be substantially axially aligned. In the illustrated embodiment, the cylinder 216 generally makes up less than 40% of the heater arrangement 110, which is made up of both the cylinder 216 and the heater chassis 218. In some embodiments, the cylinder 216 may make up less than 50%, 38%, or 30% of the heater arrangement 110. The geometry and material composition of the heater arrangement 110 may be determined using finite element analysis (FEA) to enhance or optimize heat transfer across the heater arrangement 110. That is, particular geometries of the cylinder 216 and the heater chassis 218 may be determined using FEA to enhance heater performance.

Referring again to FIG. 17, the opening 238 and the passage 248 preferably extend continuously and do not have a constant diameter therethrough. More specifically, the opening 238 comprises a first diameter d1 defined by the first interior edge 236, and a second diameter d2 defined by a second interior edge 254 of the cylinder 216, wherein the first diameter d1 is preferably smaller than the second diameter d2. Similarly, the passage 248 of the heater chassis 218 comprises a diameter d3 adjacent the lower end 222 thereof. The passage 248 adjacent the upper end 220 of the heater chassis 218 has a diameter that is substantially equivalent to the diameter d2 defined by the second interior edge 254 of the cylinder 216 such that when the upper end 220 of the heater chassis 218 abuts the second interior edge 254 of the cylinder 216, the passage 248 has a non-uniform diameter that converges toward the diameter d2 of the cylinder 216 at the second interior edge 254 to form a flush, even transition seam 255 thereacross. Alternatively, in some embodiments, the upper end 220 of the heater chassis 218 may have a diameter that is greater than or less than the diameter d2. However, preferably, the diameter d3 is larger than both the diameter d2 and the diameter d1.

Figure 20:
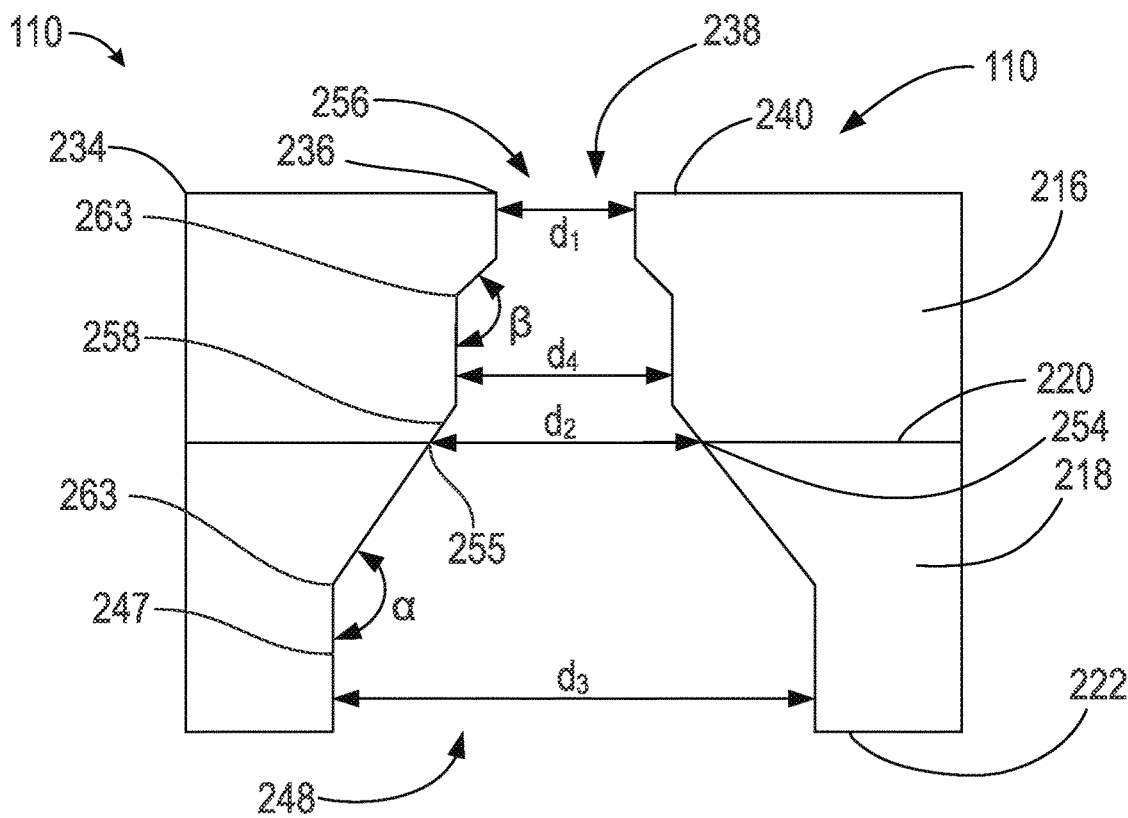
FIG. 20 is a schematic of a heater arrangement according to still another embodiment of the present disclosure.
Figure 21:
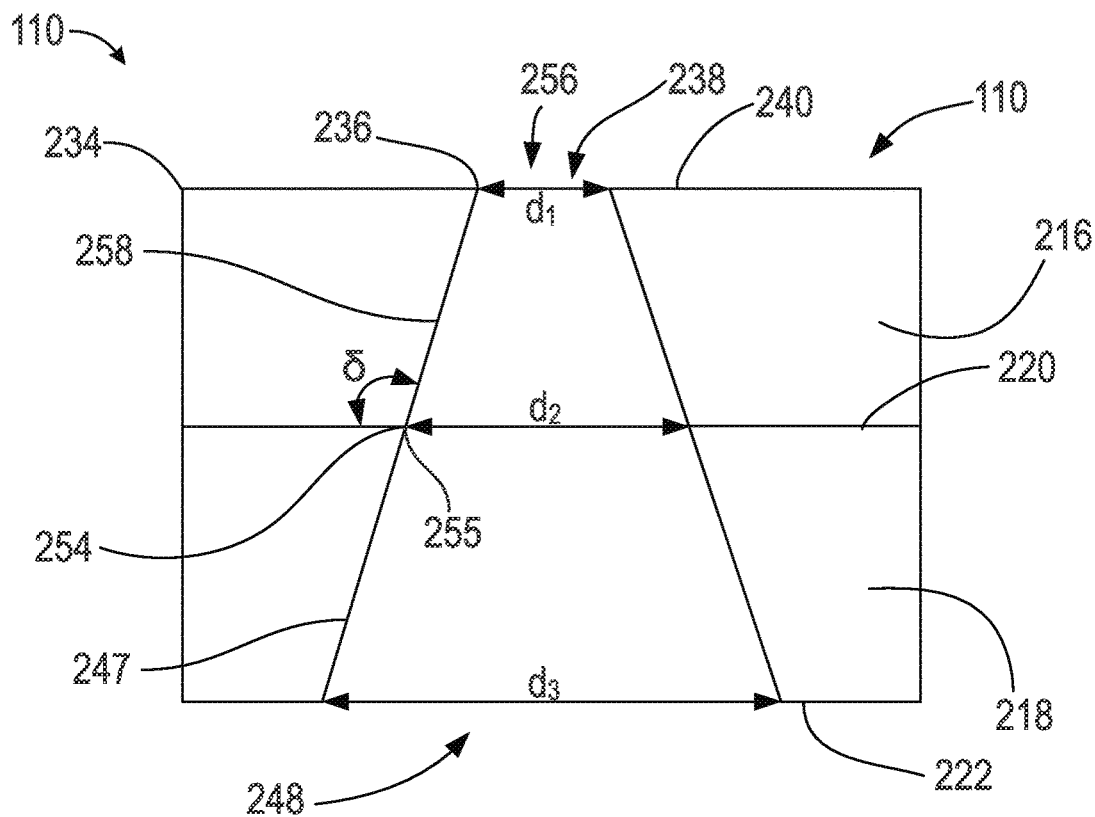
FIG. 21 is a schematic of a heater arrangement according to yet another embodiment of the present disclosure.
Figure 22:
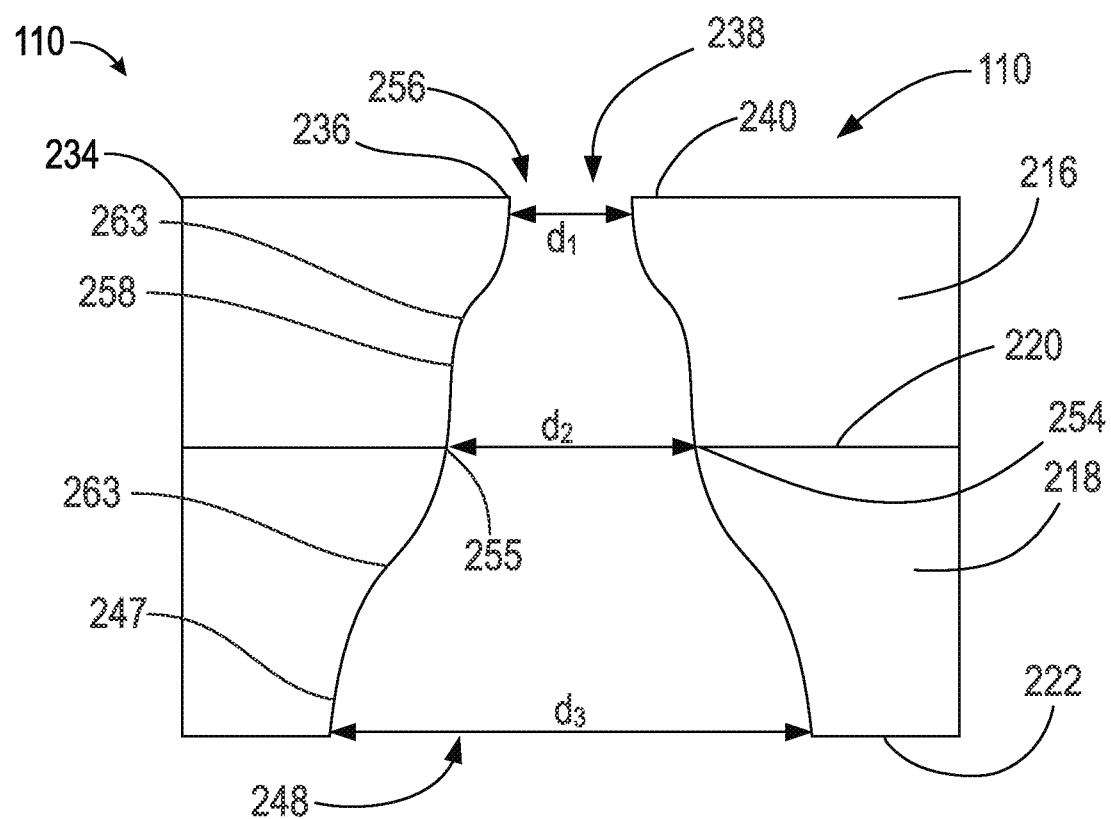
FIG. 22 is a schematic of a heater arrangement according to another embodiment of the present disclosure.
Figure 23:
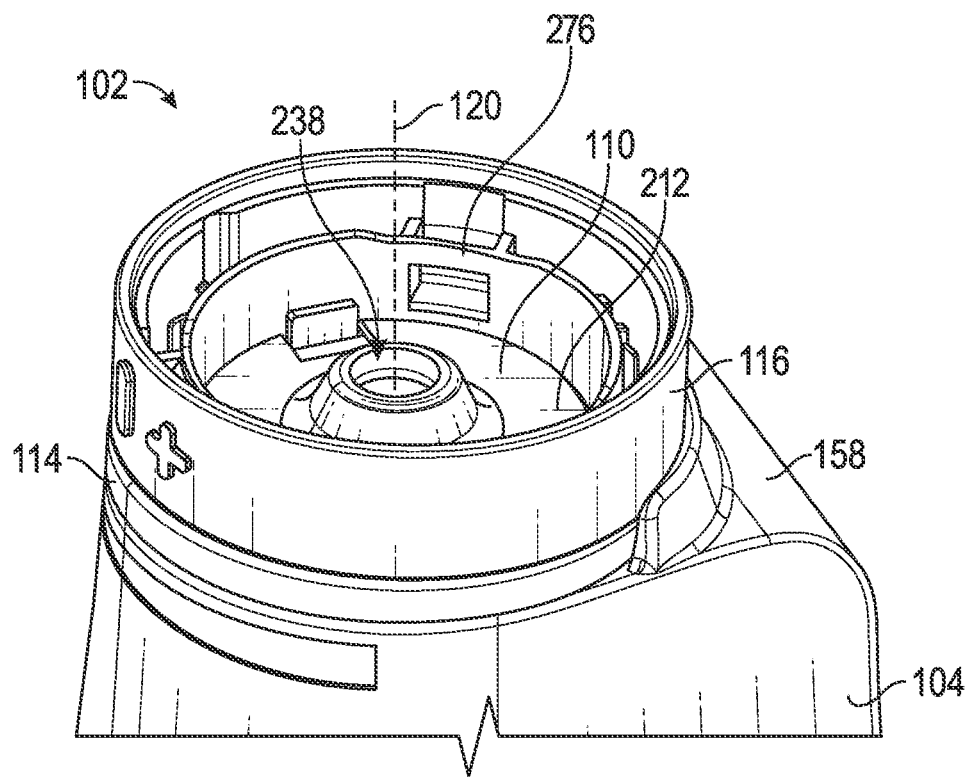
FIG. 23 is a partial isometric view of the dispensing system of FIG. 1 including the heater arrangement of FIG. 13.

As best seen in FIGS. 18-22, which illustrate example schematics of the passage 248 and the opening 238 of the heater arrangement 110, components of the heater arrangement 110 (i.e., the heater chassis 218 and the cylinder 216) are configured to define a restricting channel 256. That is, the passage 248 and the opening 238, when in axial alignment, gradually converge from the lower end 222 of the passage 248 to the first interior edge 236 of the opening 238. Differently said, the restricting channel 256 of the heater arrangement 110 restricts, tapers, or otherwise converges from the diameter d3 to the diameter d1. The diameter d3 thus is larger than the diameter d1. The restricting channel 256 may restrict in various different ways. For example, referring to FIG. 18, the restricting channel 256 may iteratively restrict using a plurality of tapered steps. More specifically, the restricting channel 256 may extend from the lower end 222 having a consistent diameter d3 for a distance of "a" mm. Then, the restricting channel 256 may converge at an angle a for "b" mm measured along the axis 120. From there, the channel 256 may extend at a uniform diameter d4 for "c" mm until it restricts again at an angle for "d" mm. The channel 256 may continue again at a substantially constant diameter ds for "e" mm until it reaches the heater chimney 242, wherein it then restricts at an angle y for "H" mm (i.e., until it reaches the first interior edge 236 having the diameter d1). Alternatively, referring to FIG. 19, the channel 256 may substantially uniformly taper at an angle 8 from the lower end 222 to the first interior edge 236, ending in the chimney 242. FIGS. 20 and 21 show two alternative configurations of the restricting channel 256 of the heater arrangement 110. FIGS. 20 and 21 are substantially similar to FIGS. 18 and 19, respectively, except that they do not end in a chimney (see, e.g., the chimney 242 of FIGS. 18 and 19). That is, the main surface 240 is substantially planar from the peripheral edge 234 to the first interior edge 236. Further, in any of the aforementioned embodiments, straight-walled, tapered portions may be replaced with curved, tapered portions, an example of which is shown in FIG. 22.

Returning to FIG. 12, when the refill 108 is attached to the dispenser 102, the wick 130 is configured to extend through the passage 248 of the heater chassis 218 and into the opening 238 of the cylinder 216. Generally, a gap, G1, is defined by a distance measured substantially perpendicularly from an outer periphery of the upper, free end 152 of the wick 130 to an inner periphery or inner wall 258 of the cylinder 216 adjacent thereto. Alternatively, the gap, G1, may be defined by an area extending radially outward from the outer periphery at the upper, free end 152 of the wick 130 to the inner periphery or inner wall 258 of the cylinder 216 adjacent thereto. Further, alternatively, the gap, G1, may be defined a volume between the outer periphery of the wick 130 to the inner periphery or inner wall 258 of the cylinder 216 that defines the opening 238 measured along a distal portion 260 of the wick 130. In some instances, the distal portion 260 of the wick 130 is defined as portions of the wick 130 received by the opening 238, and adjacent to or otherwise surrounded by the cylinder 216. That is, the distal portion 260 of the wick 130 is any portion of the wick 130 that is radially encompassed by the cylinder 216. Alternatively, in some instances, the distal portion 260 of the wick 130 may be defined as portions of the wick 130 beyond the distal edge 154 of the sheath 150. That is, the distal portion 260 would be any portion of the wick 130 that is not encompassed or otherwise radially surrounded by the sheath 150.

Still referring to FIG. 12, the gap, G1, should be large enough to allow sufficient airflow through the heater arrangement 110, but small enough to provide sufficient heat transfer to the wick 130. The gap, G1, may be between about 0.1 mm and 2.5 mm. Preferably, the gap G1 is less than 1 mm. In some embodiments, the gap G1 is less than 0.5 mm. In illustrative embodiments, the gap is substantially constant, both radially about the axis 120 and longitudinally along the axis 120 in the region at which the wick 130 and the heater arrangement 110 or the cylinder 216 overlap. In other embodiments, the gap may be non-uniform, and the values above may represent maximum, minimum, or average radial clearance amounts. For example, in an instance where the gap G1 is defined in terms of an average cross-sectional area, G1 may be the average cross-sectional area measured between the outer periphery of a distal portion 260 of the wick 130 and the inner wall 258 defining the opening 238 taken along a length of the distal portion 260 of the wick 130 and substantially perpendicularly to axis 120. In this case, e.g., G1 may be between about 10 mm$^2$ and about 40 mm$^2$. Preferably, in this case, G1 is less than 30 mm$^2$. As another example, in an instance where the gap G1 is defined in terms of an average volume measured between the outer periphery of the distal portion 260 of the wick 130 and the inner wall 258 of the cylinder 216 along the distal portion 260 of the wick 130, G1 may be between approximately 50 mm$^3$ and 250 mm$^3$ in some instances. Further, G1 may be between approximately 100 mm$^3$ and 200 mm$^3$ in some instances. In this case, G1 is preferably less than approximately 100 mm$^3$.

Returning to FIG. 17, the passage 248 of the heater chassis 218 is to be sized so that the wick 130 may easily fit therethrough. More specifically, the diameter d3 is larger than a diameter D of the distal portion 260 or the upper, free end 152 of the wick 130, such that the radial gap G1 (see FIG. 12) between the distal portion 260 of the wick 130 and the inner walls, 247, 258 allows air to flow continuously from the lower end 222 of the heater chassis 218 up through the passage 248 and the upper end 220, across the flush transition seam 255 at which an innermost point IP of the inner wall 247 of the heater chassis 218 abuts an outermost point OP of the inner wall 258 of the cylinder 216, and through the opening 238. Additionally, the opening 238 is smaller than the outer periphery of the wick 130 (i.e., the diameter d1 is smaller than the diameter D of the wick). Consequently, the wick 130 may extend through the passage 248 of the heater chassis 218 and into the opening 238 of the cylinder 216 until just below the first interior edge 236 of the cylinder 216.

Portions of the opening 238 beyond the upper, free end 152 of the wick 130 thus converge to create a venturi affect. That is, because a cross-sectional area of the passage 248 and the opening 238 converges from the lower end 222 of the heater chassis 218 toward the first interior edge 236, air flow therethough may naturally increase in velocity. Accordingly, the inner wall 247 of the heater chassis 218 and the inner wall 258 of the cylinder 216 define smooth surfaces, in accordance with the aforementioned materials used, and each of the inner wall 247 and the inner wall 258 extends obliquely away from the longitudinal axis 120 and forms inflection points 263 therealong, such as the curved or tapered portions of the restricting channel 256 illustrated in FIGS. 18, 20, and 22. Heat from the heater arrangement 110 travels inwardly through the air gap G1 toward the wick 130 through conduction and radiation and gets trapped around the wick 130, thereby increasing the overall temperature in the gap G1 and therefore in the wick 130, creating a distribution of heat around a circumference of the wick 130, and further increasing volatilization of the volatile material in the wick 130. In one aspect, heat may be distributed substantially uniformly about a circumference of the wick. Additionally, or alternatively, heat may be distributed substantially uniformly longitudinally along the wick 130 and/or the heater arrangement 110. In still another aspect, the heater arrangement 110 may apply a greater or lesser amount of heat at different longitudinal or radial portions of the wick 130, e.g., by locating the heater closer to or farther from the wick, by forming the housing 104 of more or less thermally conductive material at different longitudinal or radial positions, by adding one or more additional heaters at different locations, or by modifying the geometry of the housing 104 to be closer to or farther from the wick 130 at different locations.

Figure 24:
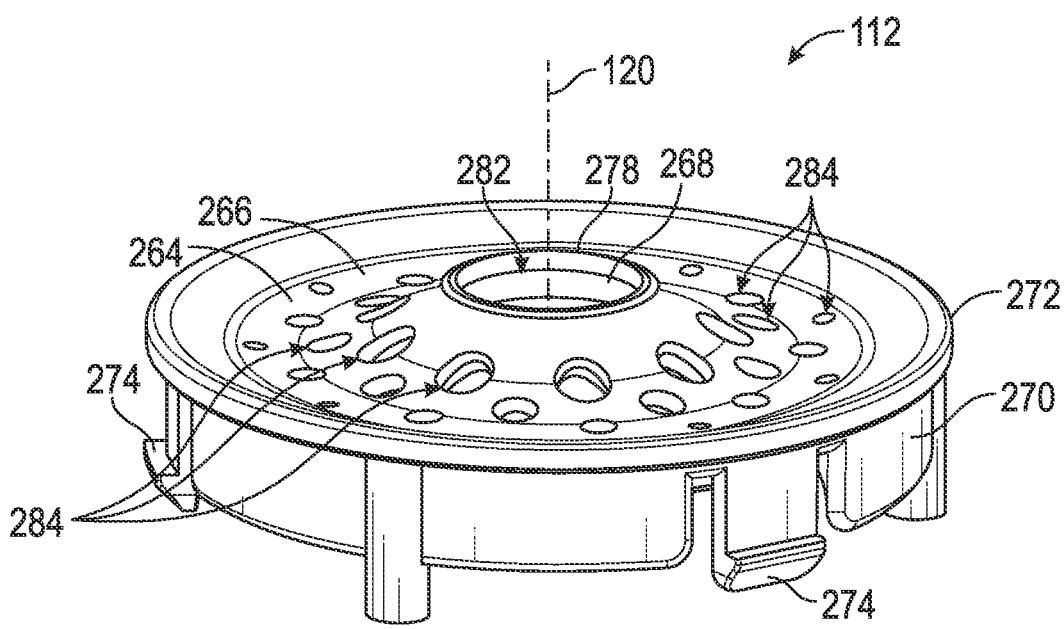
FIG. 24 is a front isometric view of a top cover according to an embodiment of the present disclosure.
Figure 25:
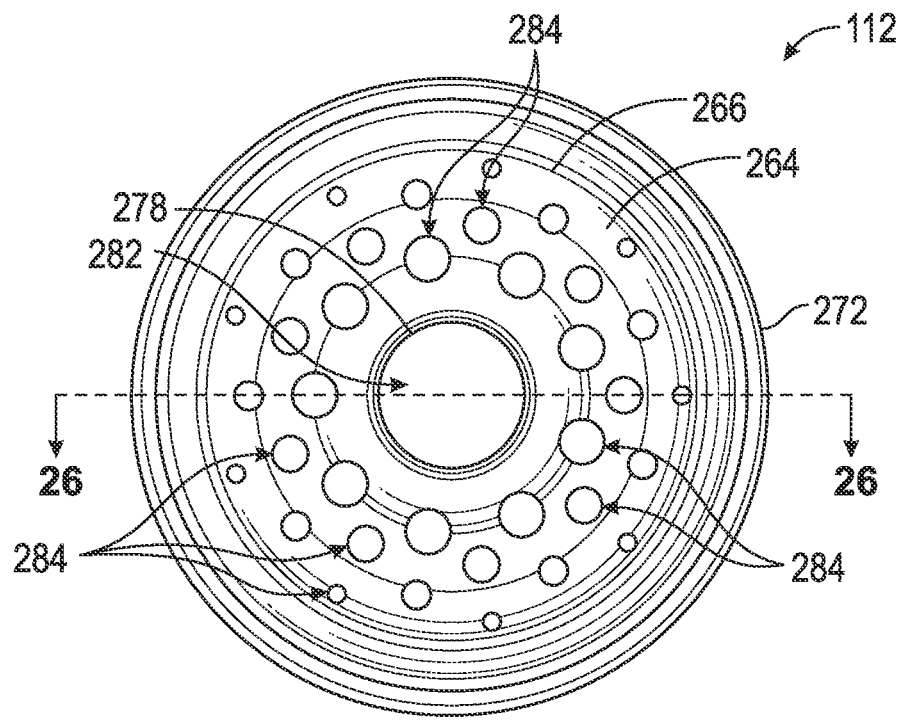
FIG. 25 is a top plan view of the top cover of FIG. 24.
Figure 26:
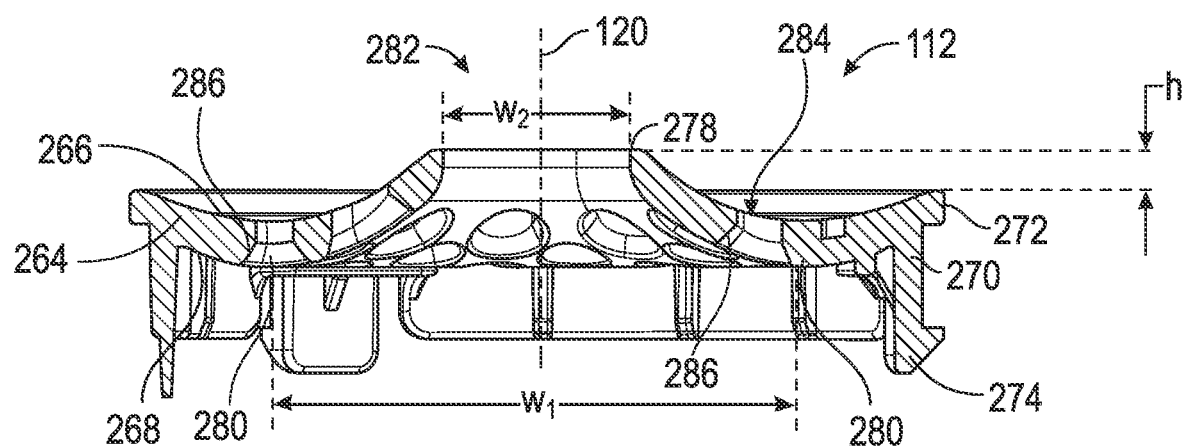
FIG. 26 is a cross-sectional view of the top cover of FIG. 25 taken across line 26-26 of FIG. 25.
Figure 27:
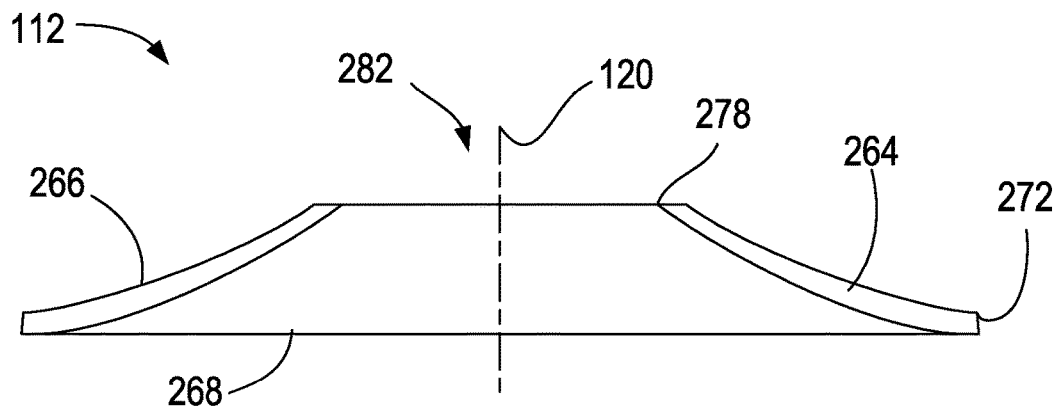
FIG. 27 is a schematic of a top cover according to another embodiment of the present disclosure.
Figure 28:
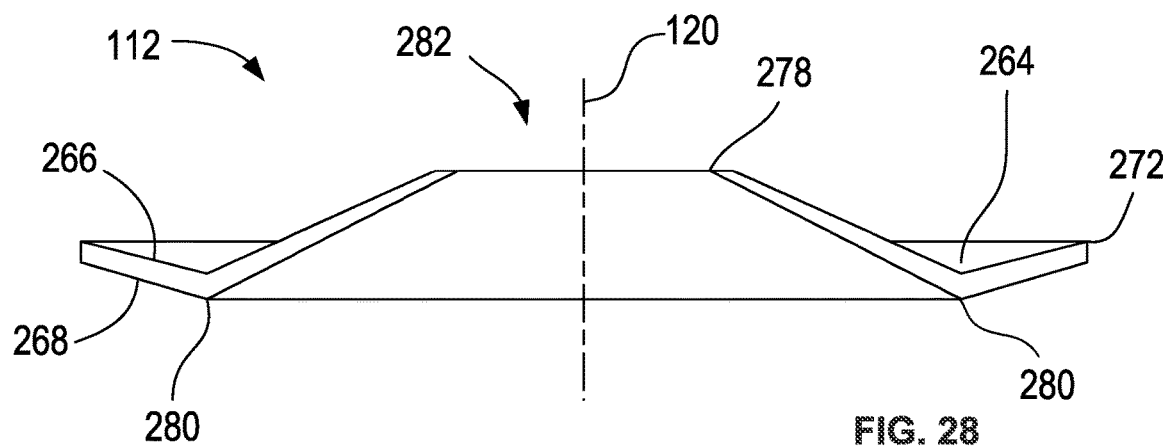
FIG. 28 is a schematic of a top cover according to still another embodiment of the present disclosure.
Figure 29:
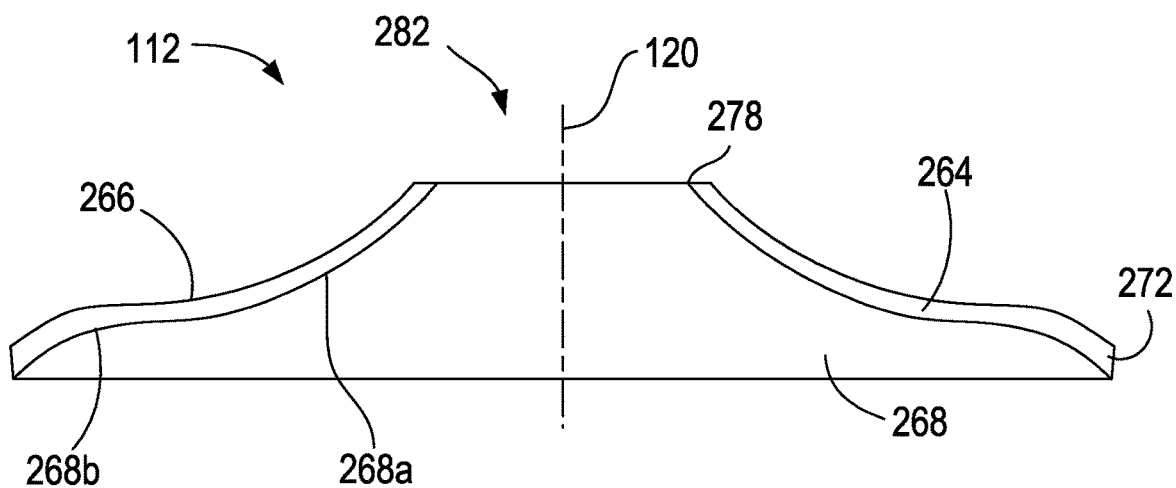
FIG. 29 is a schematic of a top cover according to yet another embodiment of the present disclosure.
Figure 30:
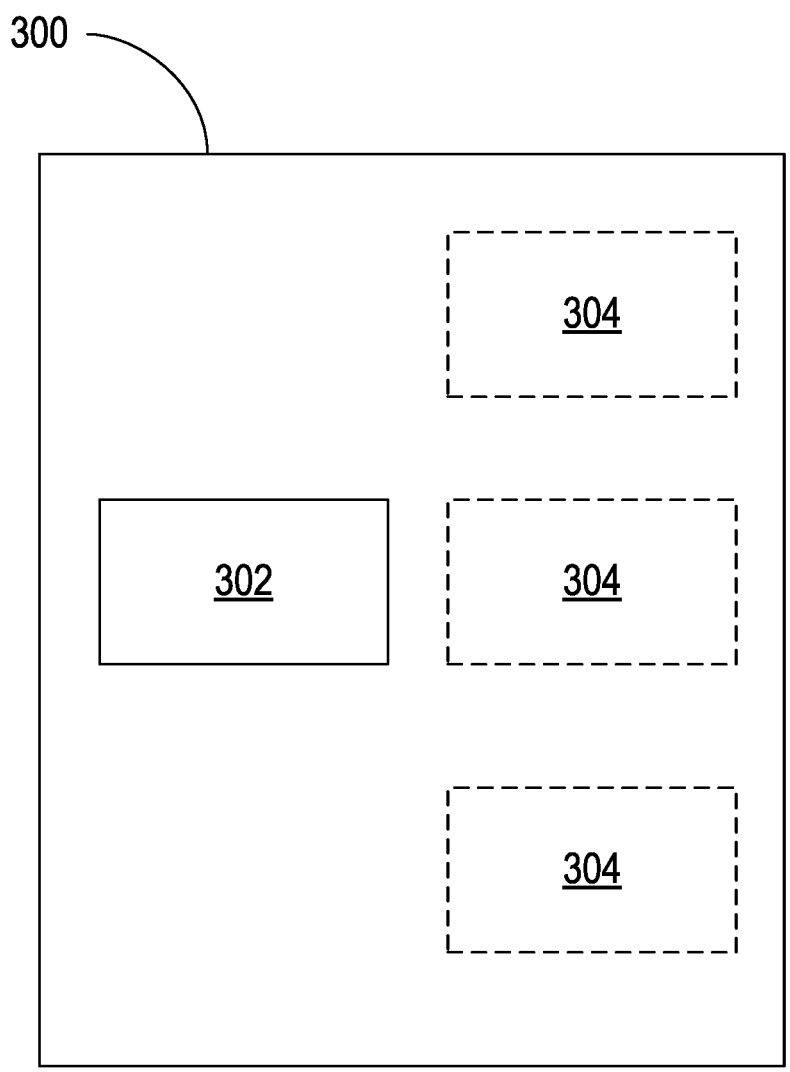
FIG. 30 is a schematic of a heater arrangement according to an embodiment of the present disclosure.

FIGS. 24-26 show various views of the top cover 112. Referring particularly to FIG. 24, the top cover 112 includes an annular wall 264 having a first surface 266, a second surface 268 (see, e.g., FIG. 26), and an annular rim 270 extending from an outer edge 272 thereof. The annular rim 270 comprises a plurality of latches 274 that are configured to be received and secured by receiving portions 276 of the control dial 116 (see, e.g., FIG. 23). In the illustrated embodiment, the top cover 112 includes three latches 274, however, alternative embodiments may include more or fewer latches.

Still referring to FIGS. 24-26, the annular wall 264 of the top cover 112 includes an inner edge 278 disposed inwardly from the outer edge 272. As best seen in FIG. 26, the outer edge 272 and the inner edge 278 are oriented on different planes so that the inner edge 278 defines an uppermost portion of the top cover 112. In the illustrated embodiment, the inner edge 278 and the outer edge 272 are spaced apart by a height "h." In some instances, the height "h" may be between 1 mm and 10 mm. In some embodiments, the height "h" may be less than 5 mm. In some embodiments, the height "h" may be less than 3 mm. Further, the second surface 268 extends from the outer edge 272 toward the inner edge 278 in a convex fashion. More specifically, the annular wall 264 extends downwardly in a first direction toward a trough 280 so that the second surface 268 is convex. From the trough 280, the second surface 268 convexly curves in a second direction until it meets the inner edge 278. Thus, the inner edge 278 defines a central aperture 282, and the second surface 268 defines a converging structure around the central aperture 282 for the emission of volatile material therethrough.

It should be understood, however, that the top cover 112 according to alternative embodiments may taper from the outer edge 272 toward the central aperture 282 and the inner edge 278 in different ways. For example, referring to FIG. 27, the trough 280 (see, e.g., FIG. 26) may be omitted so that the top cover 112 gradually curves from the outer edge 272 to the inner edge 278 in one direction. Although the second surface 268 is convex in the illustrated embodiment, the second surface 268 may be concave in other embodiments. Further, referring to FIG. 28, the annular wall 264 may angle from the outer edge 272 or the trough 280 to the inner edge 278. That is, the annular wall 264 is generally straight-line from the outer edge 272 to the trough 280, and from the trough 280 to the inner edge 278 to define a funnel-like structure for the emission of volatile material through the central aperture 282. Furthermore, referring to FIG. 29, the annular wall 264 may curve in multiple directions as it extends from the outer edge 272 to the inner edge 278. More specifically, the second surface 268 may include a convex portion 268a and a concave portion 268b that define a smooth curved surface to direct volatile material through the central aperture 282. Preferably, the convex portion 268a is adjacent the inner edge 278 and the concave portion 268b is adjacent the outer edge 272.

Returning to FIG. 26, in the present embodiment, the first surface 266 of the top cover 112 projects opposite the second surface 268 and may generally track the same shape as the second surface 268. That is, the first surface 266 may extend from the outer edge 272 toward the inner edge 278 while curving in the first direction along the axis 120 that is opposite from the inner edge 278 until the trough 280. From the trough 280, the first surface 266 may gradually curve in the second direction along the axis 120 that is opposite from the first direction until it meets the inner edge 278. Thus, the first surface 266 is generally concave.

Similar to the heater arrangement 110 discussed above (see, e.g., FIG. 17), still referring to FIG. 26, using a converging configuration helps to concentrate and guide a vapor out of a dispenser. That is, because the second surface 268 gradually curves from a diameter $w_1$ to a diameter $w_2$ defined by the central aperture 282, the top cover 112 generally defines a converging outlet to provide a venturi effect on the vapor flow out of the dispenser. In the illustrated embodiment, the diameter $w_1$ is the diameter defined by the trough 280. Preferably, the diameter $w_2$ is between 50% and 80% of the diameter $w_1$. In some instances, the diameter $w_2$ is between 60% and 70% of the diameter $w_1$. Further, preferably, the second surface 268 is generally smooth. The second surface 268 thus is generally a continuous curve from the outer edge 272 to the inner edge 278. As a result, a venturi affect is established, which ultimately increases speed of the vapor flow therethrough to enhance vapor release to a surrounding area.

Referring now to FIG. 25, the annular wall 264 further defines a plurality of apertures 284 arranged around the central aperture 282. In the embodiment illustrated, the plurality of apertures 284 decrease in size as they are positioned farther from the central aperture 282. That is, the plurality of apertures 284 proximate the outer edge 272 are smaller than the plurality of apertures 284 proximate the inner edge 278. The plurality of apertures 284 may be incorporated to provide venting capabilities and alternative routes for the emission of volatile material therethrough, thereby prevent recirculation of the vapor within the housing, which is a significant cause of condensation. Although the embodiment illustrated comprises a plurality of apertures, additional embodiments of the present disclosure may include a top cover having more, fewer, or no apertures in a variety of designs and configurations. Further, the plurality of apertures 284 may include chamfered, filleted, or straight edges. More particularly, in the illustrated embodiment, the plurality of apertures 284 include chamfered edges 286 to minimize disturbing vapor flow out of the housing (i.e., the plume). Preferably, the plurality of apertures 284 include the chamfered edges 286 adjacent the second surface 268.

Furthermore, dispensers according to embodiments of the present disclosure experience enhanced airflow control. For example, referring to FIG. 12, the relationship between the heater arrangement 110, the wick 130, and the housing 104, in addition to the presence of the plurality of apertures 284 having chamfered edges 286, results in reduced air recirculation within the internal cavity 106, which ultimately reduces a potential for condensation formation within the housing 104. Further, minimal recirculation allows for enhanced release of the volatile material to the surroundings, which may result in a visibly strong and consistent plume.

Still referring to FIG. 12, again, the heater arrangement 110 is configured to receive the wick 130 and, thus, convert localized heating of the resistor 214 to a radiant heat source surrounding the wick 130 on a plurality of sides thereof. More specifically, the wick 130 may extend through the passage 248 of the heater chassis 218 into the opening 238 of the cylinder 216. The heater arrangement 110, generally, and the resistor 214, in particular, are disposed proximate the upper, free end 152 of the wick 130, which leads to enhanced evaporation of the fluid drawn from the container 126 by the wick 130. In one embodiment, also as seen in FIG. 12, the heater arrangement 110 extends longitudinally above the upper, free end 152 of the wick 130 in order to continue heating volatilized material, even after the material has dispersed from the wick 130. Therefore, as a volatized material exits the heater arrangement 110, it will continue to be heated within the internal cavity 106, which can actually increase the energy in the volatized material and, thus, velocity of the volatized material outside of the dispenser 102. This configuration also may permit the heater to be disposed closer to the central aperture 282 of the top cover 112, again retaining the volatilized material at an elevated temperature while it travels through the internal cavity 106, thereby decreasing condensation of the material and promoting dispersion of the volatized material into the environment.

The heater arrangement 110 according to the present disclosure results in enhanced heating of the wick 130. Particularly, the heater arrangement 110 results in a uniform and consistent heating of the wick 130 as compared to existing dispensers. This improvement is a result of the design choices described above, particularly the result of using a ceramic metal composite having a high metal content (e.g., aluminum) therein. By embedding the resistor 214 in a highly conductive material, heat from the resistor 214 easily distributes throughout the cylinder 216 to create a substantially uniform temperature profile, which positively impacts the overall performance of the dispenser 102. For example, according to the present embodiment, the main surface 240 of the cylinder 216 experiences a temperature gradient (or temperature difference) of less than 20° C. In some embodiments, the main surface 240 of the cylinder 216 experiences a temperature gradient (or temperature difference) of less than 15° C. This temperature gradient is significantly reduced compared to existing dispensers, which may experience temperature gradients of 20° C. to 40° C. Temperature gradients of such magnitude can interrupt a vapor flow out of a dispenser. More specifically, a plume being dispensed by the dispenser can be pulled or drawn toward a warm side of the heater arrangement, which can cause air recirculation inside the internal cavity and subsequent condensation formation.

Referring again to FIG. 17, it is to be understood that the performance of the heater arrangement 110 may be achieved using a variety of heat sources. That is, the heating element 212 having the single resistor 214 is not the only heat source that, combined with aspects of the present disclosure, can result in enhanced heater performance. For example, referring now to FIG. 30, a heater arrangement 300 according to an embodiment of the present disclosure generally includes at least one heat source 302, which may be a resistor (such as, e.g., resistor 214 shown in FIGS. 14 and 17), an embedded wire, or any other heat source that is known in the art. However, embodiments of the present disclosure may use more than one heat source. For example, the heater arrangement 300 may include the heat source 302 in combination with one or more additional heat sources 304. More specifically, the heat source 302 of the heater arrangement 300 may be a resistor, and the heat sources 304 may be additional resistors. These resistors may be distributed throughout the heater arrangement 300 in a number of ways, such as, for example, circumferentially, longitudinally, laterally, etc. As another example, the heat source 302 of the heater arrangement 300 may be an embedded wire, and the heat sources 304 may be a combination of resistors and/or embedded wires. Again, these heat sources 302, 304 may be disposed throughout the heater arrangement 300 circumferentially, longitudinally, laterally, etc. Further, in some embodiments, the heat sources 302, 304 of the heater arrangement 300 may be discrete resistors mounted to a printed circuit board. Therefore, heater arrangements according to embodiments of the present disclosure may incorporate any heat source or combination of heat sources that are known in the art.

An experiment was conducted to compare performance of the heater arrangement 110 with a diffusion element from an existing dispenser. Three devices were tested. A first device ("Device 1") is similar to the device described herein with respect to FIGS. 1-26 and included the heater arrangement 110 as shown and described with respect to FIGS. 12-17 and further included the top cover 112 as shown and described with respect to FIGS. 23-26. A second device ("Device 2") is a device currently sold by S. C. Johnson & Son, Inc. under the name Glade® Plug-Ins® and detailed in Belongia et al. U.S. Pat. Pub. 2012/0275772. A third device ("Device 3") is another plug-in dispenser known and sold in the market.

All three devices were tested with a refill filled to an equal level of a consistent formula. The testing facility was an environmentally controlled room maintained at a temperature of 70° Fahrenheit (+/−2° F.). Each device was operated at their respective intended operating power. The results of the experiment are shown in Table 1 below.

TABLE 1

| | Duration (Days) | Total Volatile Material Released (g) | Power Input (Watts) | Efficiency Factor (mg/hr/Watt) |
|---|---|---|---|---|
| Device 1 | 11.3 | 17.8 | 1.8 | 36.5 |
| Device 2 | 19.3 | 17.8 | 2.2 | 17.5 |
| Device 3 | 22 | 17.8 | 1.7 | 19.8 |

Referring to Table 1 above, Device 1 required less power input to release the volatile material than required by Device 2 and Device 3. Further, Device 1 demonstrated a substantial increase in volatile material emanation, which resulted in the shortened duration required to release 17.8 grams ("g") of the volatile material. Again, Device 1 closely resembles the dispensing system 100 described herein with respect to FIGS. 1-26. Therefore, the heater arrangement 110 described above results in enhanced heater performance.

In the analysis phase of the experiment, after the testing was completed and the appropriate data was collected, a device efficiency factor was calculated for each device using the equation:

Device Efficiency Factor=Average Overall Hourly Weight Loss/Power

Because both devices are designed to operate at a different power, the device efficiency factor is used to compare overall performance of the two devices. The calculated device efficiency factor is shown in table 1 above. In summary, Device 1 has a significantly higher emanation rate per unit watt than Device 2 and Device 3. In fact, the device efficiency factor of the Device 1 is more than twice the device efficiency factor of Device 2 and almost twice the device efficiency factor of Device 3. Differently said, the amount of power necessary to operate Device 1 is a fraction of the power necessary for Device 2 and Device 3 to achieve the same or a greater emanation rate. Consequently, Device 1 experiences energy savings and increased efficiency. This enhanced performance is a result of the design choices discussed above, particularly, e.g., material choice for the heater arrangement 110, geometry of the heater arrangement 110, geometry of the top cover 112, and arrangement or proximity of the wick 130 to the heater arrangement 110. In the illustrated embodiments, the efficiency factor of the heaters disclosed herein is greater than or equal to about 25. In other illustrative embodiments, the efficiency factor of one or more of the heaters disclosed herein is greater than or equal to about 40, greater than or equal to about 45, or greater than or equal to about 50.

INDUSTRIAL APPLICABILITY

Numerous modifications to the present invention will be apparent to those skilled in the art in view of the foregoing description. Accordingly, this description is to be construed as illustrative only and is presented for the purpose of enabling those skilled in the art to make and use the invention. The exclusive rights to all modifications which come within the scope of the appended claims are reserved.

We claim:

1. A volatile material dispenser, comprising:
   a housing that defines a longitudinal axis and is configured to receive a refill containing a volatile material and a wick;
   a cylinder that includes an inner wall that defines an opening and an interior edge, wherein a resistor is embedded in the cylinder; and
   a heater chassis that includes an inner wall that defines a passage between an upper end and a lower end,
   wherein the upper end of the heater chassis abuts the interior edge of the cylinder, and
   wherein the inner wall of the cylinder extends away from the longitudinal axis at a first angle and the inner wall of the heater chassis extends away from the longitudinal axis at a second angle.

2. The volatile material dispenser of claim 1, wherein the first angle and the second angle are identical.

3. The volatile material dispenser of claim 1, wherein the first angle and the second angle are different.

4. The volatile material dispenser of claim 1, wherein the inner wall of the cylinder includes at least one inflection point between the opening and the interior edge.

5. The volatile material dispenser of claim 1, wherein the inner wall of the heater chassis includes at least one inflection point between the upper end and the lower end.

6. The volatile material dispenser of claim 1, wherein a first diameter of the passage at the upper end is smaller than a second diameter of the passage at the lower end.

7. The volatile material dispenser of claim 1, wherein the dispenser is configured such that, when the refill is received within the housing, the opening of the cylinder is axially aligned with the wick, and a radial gap is formed between the cylinder and a distal portion of the wick.

8. The volatile material dispenser of claim 7, wherein the opening of the cylinder is smaller than an outer diameter of the distal portion of the wick.

9. The volatile material dispenser of claim 1, wherein the cylinder and the heater chassis are formed of different materials from one another.

10. The volatile material dispenser of claim 9, wherein the heater chassis is formed of a material that includes nylon.

11. The volatile material dispenser of claim 1, wherein the cylinder is formed of a material that includes metal.

12. The volatile material dispenser of claim 11, wherein the material of the cylinder further comprises ceramic.

13. The volatile material dispenser of claim 1, wherein the inner wall of the heater chassis extends continuously from the lower end to the upper end.

14. The volatile material dispenser of claim 13, wherein the cylinder and the heater chassis are coupled to form a heater arrangement within the housing, and wherein the passage of the heater chassis extends at least 40% of a total height of the heater arrangement.

15. A volatile material dispenser, comprising:
    a housing that defines a longitudinal axis and is configured to receive a refill containing a volatile material and a wick;
    a cylinder that includes an inner wall that defines an opening and an interior edge, wherein a resistor is embedded in the cylinder; and
    a heater chassis that includes an inner wall that defines a passage between an upper end and a lower end,
    wherein an interior edge of the cylinder is configured to abut the upper end of the heater chassis, and
    wherein the passage of the heater chassis has a non-uniform diameter that converges toward a diameter of the interior edge of the cylinder.

16. The volatile material dispenser of claim 15, wherein the diameter of the passage adjacent to the upper end is substantially equivalent to the diameter defined by the interior edge of the cylinder.

17. The volatile material dispenser of claim 15, wherein the passage gradually narrows between the upper end and a lower end of the heater chassis.

18. The volatile material dispenser of claim 17, wherein the inner wall of the cylinder and the inner wall of the heater chassis are flush across the interior edge and the upper end.

19. The volatile material dispenser of claim 15, wherein the passage of the heater chassis is continuous and unobstructed by a protrusion extending inwardly from the inner wall.

20. The volatile material dispenser of claim 15, wherein the inner wall of the passage and the inner wall of the cylinder are smooth.

21. The volatile material dispenser of claim 15, wherein the cylinder is formed of at least one of a ceramic material or a metal material.

22. The volatile material dispenser of claim 21, wherein the heater chassis is formed of a nylon material.

23. The volatile material dispenser of claim 15, wherein the cylinder and the heater chassis are coupled to form a heater arrangement, and wherein, when the refill is received in the housing, a radial gap is formed between the heater arrangement and a distal portion of the wick, the radial gap being non-uniform along the longitudinal axis.

24. A volatile material dispenser, comprising:
    a housing that defines a longitudinal axis and is configured to receive a refill containing a volatile material and a wick;
    a cylinder that includes an inner wall that defines an opening and an interior edge opposite the opening, wherein a resistor is embedded in the cylinder; and
    a heater chassis that includes an inner wall that defines a passage between an upper end and a lower end,
    wherein an interior edge of the cylinder is configured to abut the upper end of the heater chassis, and
    wherein the inner wall of the heater chassis at the upper end defines a substantially flush seam with the inner wall of the cylinder at the interior edge.

25. The volatile material dispenser of claim 24, wherein the inner wall of the cylinder defines at least one inflection point.

26. The volatile material dispenser of claim 25, wherein the opening of the cylinder is smaller than a diameter at the interior edge.

27. The volatile material dispenser of claim 26, wherein the diameter at the interior edge is smaller than a diameter of the passage at the lower end of the heater chassis.

28. The volatile material dispenser of claim 27, wherein the passage of the heater chassis converges toward a diameter of the interior edge of the cylinder.

29. The volatile material dispenser of claim 24, wherein, when the wick is received by the housing, a radial gap is defined between the inner wall of the heater chassis and an outer diameter of the wick, and wherein the radial gap is non-uniform between the upper end and the lower end.

30. A volatile material dispenser, comprising:
a housing that defines a longitudinal axis and is configured to receive a refill containing a volatile material and a wick;
a heater comprising a resistor; and
a chassis supporting the heater, wherein the chassis defines a passage about the longitudinal axis, the passage being at least partially defined by an inner wall that is disposed at an oblique angle relative to the longitudinal axis,
wherein, when the refill is received by the housing, a radial gap is formed within the passage about an outer diameter of a distal portion of the wick, and
wherein the radial gap is non-uniform along the longitudinal axis.

31. The volatile material dispenser of claim 30, wherein the inner wall of the chassis includes at least one of a curved portion or a tapered portion.

32. The volatile material dispenser of claim 31, wherein the inner wall of the chassis tapers inwardly toward an interior edge of the heater.

33. The volatile material dispenser of claim 32, wherein the passage converges from a lower end of the chassis toward the interior edge of the heater.

34. The volatile material dispenser of claim 30, wherein a main surface of the heater extends toward a first interior edge that defines an opening, wherein a second interior edge of the heater abuts an upper end of the chassis, and wherein the main surface of the heater is coupled to the chassis.

35. The volatile material dispenser of claim 34, wherein the opening has a diameter that is smaller than a diameter defined by the second interior edge.

36. The volatile material dispenser of claim 30, wherein the heater comprises less than 50% of a volume of a heater arrangement comprising the heater and the chassis.

37. A volatile material dispenser, comprising:
a housing that defines a longitudinal axis and is configured to receive a refill containing a volatile material and a wick;
a heater comprising a resistor; and
a chassis supporting the heater, wherein the chassis defines a passage about the longitudinal axis, the passage being at least partially defined by an inner wall that is disposed at an oblique angle relative to the longitudinal axis,
wherein the inner wall of the chassis defines an innermost point relative to the longitudinal axis and an inner wall of the heater defines an outermost point relative to the longitudinal axis, and wherein the innermost point and the outermost point are disposed a radial distance about the longitudinal axis.

38. The volatile material dispenser of claim 37, wherein, when the refill is received by the housing, a distal portion of the wick is received within the passage and a radial gap is formed between an outer diameter of the distal portion of the wick and the heater, wherein the radial gap is non-uniform along the longitudinal axis.

39. The volatile material dispenser of claim 37, wherein, when the refill is received by the housing, a distal portion of the wick is received within the passage and a radial gap is formed between an outer diameter of the distal portion of the wick and the chassis, wherein the radial gap is non-uniform along the longitudinal axis.

40. The volatile material dispenser of claim 37, wherein the heater comprises a ceramic metal composite material and the chassis comprises a nylon material.

\* \* \* \* \*